US012765964B2

(12) United States Patent
Soto

(10) Patent No.: US 12,765,964 B2
(45) Date of Patent: Oct. 20, 2026

(54) QUICK-CONNECT MOUNTING SYSTEM FOR SURGICAL COMPONENTS

(71) Applicant: MAKO Surgical Corp., Weston, FL (US)

(72) Inventor: Victor Soto, Coral Gables, FL (US)

(73) Assignee: MAKO Surgical Corp., Weston, FL (US)

( * ) Notice: Subject to any disclaimer, the term of this patent is extended or adjusted under 35 U.S.C. 154(b) by 682 days.

(21) Appl. No.: 18/104,687

(22) Filed: Feb. 1, 2023

(65) Prior Publication Data

US 2023/0240793 A1 Aug. 3, 2023

Related U.S. Application Data

(60) Provisional application No. 63/305,781, filed on Feb. 2, 2022.

(51) Int. Cl.

*F16B 2/16* (2006.01)
*A61B 90/50* (2016.01)
*F16B 2/18* (2006.01)

(52) U.S. Cl.

CPC ................ *A61B 90/50* (2016.02); *F16B 2/16* (2013.01); *F16B 2/18* (2013.01); *Y10T 403/592* (2015.01)

(58) Field of Classification Search

CPC ............................... F16B 2/16; Y10T 403/592
See application file for complete search history.

(56) References Cited

U.S. PATENT DOCUMENTS

| | | | |
|---|---|---|---|
| 2,290,215 A | 7/1942 | Stenberg | |
| 3,430,305 A | 3/1969 | Geffner | |
| 4,815,780 A | 3/1989 | Obrist | |

(Continued)

FOREIGN PATENT DOCUMENTS

| | | | |
|---|---|---|---|
| GB | 867133 A * | 5/1961 | ................ F16B 2/16 |
| GB | 2447239 A | 9/2008 | |

(Continued)

OTHER PUBLICATIONS

English language abstract and machine-assisted English translation for JP 6321852 B1 extracted from espacenet.com database on Feb. 2, 2023, 9 pages.

(Continued)

*Primary Examiner* — Michael P Ferguson
(74) *Attorney, Agent, or Firm* — Howard & Howard Attorneys PLLC

(57) ABSTRACT

A mounting system for mounting two components together includes a first mounting portion having a first body. A lip and a push pin that is spaced from the lip extend from the first body. The mounting system includes a second mounting portion for coupling to the first mounting portion. The second mounting portion has a second body defining a bore. Retainers are moveable within openings of the second body. A loading assembly is disposed in the bore of the second body. The loading assembly is moveable to a first state. In the first state, the loading assembly moves the retainers to a coupling position where each retainer extends through one opening beyond an outer surface of the second body. In the coupling position, each retainer abuts the lip of the first mounting portion to secure the mounting portions together.

17 Claims, 15 Drawing Sheets

(56) References Cited

U.S. PATENT DOCUMENTS 4,836,068 A * 6/1989 Erickson .............. B23B 29/046 403/322.2
4,906,123 A 3/1990 Weskamp et al.
5,211,501 A 5/1993 Nakamura et al.
5,692,851 A * 12/1997 Pace .................... F15B 15/261 403/322.2
5,876,328 A 3/1999 Fox et al.
6,398,279 B1 6/2002 Kikut
6,416,248 B1 7/2002 Clark
6,641,128 B2 11/2003 Fries
6,729,589 B2 5/2004 Shelef
6,746,172 B2 6/2004 Culpepper
6,955,138 B2 10/2005 DeBien
7,122,032 B2 10/2006 Shinmura et al.
7,162,978 B2 1/2007 Debien
7,173,779 B2 2/2007 Shelef
7,252,453 B1 8/2007 Little
7,303,195 B2 12/2007 Nie
7,331,967 B2 2/2008 Lee et al.
7,422,107 B2 9/2008 Burns et al.
7,431,531 B2 10/2008 Carnevali
7,506,876 B1 3/2009 Roopnarine
7,559,265 B2 7/2009 Mizuno
7,699,855 B2 4/2010 Anderson et al.
7,886,743 B2 2/2011 Cooper et al.
7,947,050 B2 5/2011 Lee et al.
7,963,913 B2 6/2011 Devengenzo et al.
8,005,570 B2 * 8/2011 Gloden .................. B23B 31/30 403/322.2
8,074,657 B2 12/2011 Scott et al.
8,202,278 B2 6/2012 Orban, III et al.
8,206,406 B2 6/2012 Orban, III
8,209,840 B2 7/2012 Norton
8,220,468 B2 7/2012 Cooper et al.
8,277,505 B1 10/2012 Doty
8,413,948 B2 4/2013 Kemeny
8,460,277 B2 6/2013 Suarez et al.
8,500,132 B2 8/2013 Norton
8,529,582 B2 9/2013 Devengenzo et al.
8,533,930 B2 9/2013 Norton
8,601,667 B2 12/2013 Norton
8,602,031 B2 12/2013 Reis et al.
8,651,764 B2 * 2/2014 Lin ...................... F16B 21/165 81/177.85
8,672,922 B2 3/2014 Loh et al.
8,720,448 B2 5/2014 Reis et al.
8,747,288 B2 6/2014 Strotzer et al.
8,857,821 B2 10/2014 Norton et al.
8,985,593 B1 3/2015 Gao
8,992,113 B2 3/2015 Campagna et al.
9,008,757 B2 4/2015 Wu
9,119,655 B2 9/2015 Bowling et al.
9,151,343 B2 10/2015 Norton
9,180,527 B2 11/2015 Haimer
9,194,531 B2 11/2015 Shelef et al.
9,204,933 B2 12/2015 Reis et al.
9,254,572 B2 2/2016 Strotzer
9,339,342 B2 5/2016 Prisco et al.
9,439,732 B2 9/2016 Devengenzo et al.
9,539,060 B2 1/2017 Lightcap et al.
9,566,121 B2 2/2017 Staunton et al.
9,566,122 B2 2/2017 Bowling et al.
9,687,312 B2 6/2017 Dachs, II et al.
9,713,509 B2 7/2017 Schuh et al.
9,714,737 B2 7/2017 Nishikawa
9,937,058 B2 4/2018 Axelson, Jr. et al.
9,981,391 B2 5/2018 Kalb et al.
9,993,313 B2 6/2018 Schuh et al.
10,004,562 B2 6/2018 Kostrzewski et al.
10,022,193 B2 7/2018 Cooper et al.
10,045,828 B2 8/2018 Dachs, II et al.
10,046,465 B2 8/2018 Goto et al.
10,047,908 B1 8/2018 Bohle, II et al.
10,052,761 B2 8/2018 Langenfeld
10,076,844 B2 9/2018 Rizk
10,105,855 B2 10/2018 Kalb et al.
10,136,954 B2 11/2018 Johnson et al.
10,151,423 B2 12/2018 Shelef et al.
10,231,791 B2 3/2019 LeBoeuf, II et al.
10,265,869 B2 4/2019 Lohmeier et al.
10,271,911 B2 4/2019 Cooper et al.
10,342,625 B2 7/2019 Loh et al.
10,357,324 B2 7/2019 Flatt et al.
10,537,400 B2 1/2020 Dachs, II et al.
10,582,980 B2 3/2020 Scheib et al.
10,603,126 B2 3/2020 Karguth et al.
10,624,710 B2 4/2020 Crawford et al.
10,722,223 B2 7/2020 Wehrli et al.
10,731,687 B2 8/2020 Ponzer et al.
10,736,706 B2 8/2020 Scheib
10,806,539 B1 10/2020 Richter et al.
11,096,754 B2 8/2021 Soto et al.
11,117,197 B2 9/2021 Lindenmann et al.
2003/0083673 A1 5/2003 Tierney et al.
2006/0016061 A1 1/2006 Shelef
2006/0232837 A1 10/2006 Shelef
2007/0231063 A1 10/2007 Tsutsumi et al.
2008/0119339 A1 5/2008 Oliver
2008/0182738 A1 7/2008 Grunke et al.
2009/0051094 A1 2/2009 Sandmeier
2009/0226249 A1 * 9/2009 Yeh ......................... B25J 15/00 403/326
2009/0306499 A1 12/2009 Van Vorhis et al.
2009/0322041 A1 12/2009 Norton
2010/0166496 A1 7/2010 Bennett et al.
2010/0170519 A1 7/2010 Romo et al.
2010/0196113 A1 8/2010 Erickson et al.
2010/0268249 A1 10/2010 Stuart
2010/0268250 A1 10/2010 Stuart et al.
2011/0015650 A1 1/2011 Choi et al.
2011/0154645 A1 6/2011 Morgan
2011/0277775 A1 11/2011 Holop et al.
2012/0252646 A1 10/2012 Norton
2012/0301067 A1 11/2012 Morgan
2013/0168913 A1 7/2013 Schluessel
2016/0059424 A1 3/2016 Zachary et al.
2016/0184036 A1 6/2016 Solomon et al.
2016/0184037 A1 6/2016 Cooper et al.
2016/0220320 A1 8/2016 Crawford et al.
2016/0235493 A1 8/2016 LeBoeuf, II et al.
2016/0236357 A1 8/2016 Kalb et al.
2016/0256225 A1 9/2016 Crawford et al.
2016/0278875 A1 9/2016 Crawford et al.
2016/0338783 A1 11/2016 Romo et al.
2017/0007334 A1 1/2017 Crawford et al.
2017/0020630 A1 1/2017 Johnson et al.
2017/0071691 A1 3/2017 Crawford et al.
2017/0079727 A1 3/2017 Crawford et al.
2017/0119339 A1 5/2017 Johnson et al.
2017/0144230 A1 5/2017 Rosso et al.
2017/0165012 A1 6/2017 Chaplin et al.
2017/0172669 A1 6/2017 Berkowitz et al.
2017/0252114 A1 9/2017 Crawford et al.
2017/0258535 A1 9/2017 Crawford et al.
2017/0265774 A1 9/2017 Johnson et al.
2017/0312039 A1 11/2017 Crawford et al.
2017/0333136 A1 11/2017 Hladio et al.
2017/0348063 A1 12/2017 Braun et al.
2017/0354468 A1 12/2017 Johnson et al.
2018/0000472 A1 1/2018 Beira
2018/0064497 A1 3/2018 Hussain et al.
2018/0110576 A1 4/2018 Kopp
2018/0125597 A1 5/2018 Gogarty et al.
2018/0132839 A1 5/2018 Friedrich et al.
2018/0147018 A1 5/2018 Crawford et al.
2018/0168752 A1 6/2018 Scheib et al.
2018/0168753 A1 6/2018 Scheib et al.
2018/0168761 A1 6/2018 Vargas et al.
2018/0168762 A1 6/2018 Scheib et al.
2018/0168763 A1 6/2018 Scheib et al.
2018/0214221 A1 8/2018 Crawford et al.
2018/0221098 A1 8/2018 Forsyth et al.
2018/0256259 A1 9/2018 Crawford
2018/0271604 A1 9/2018 Grout et al.

(56) References Cited

U.S. PATENT DOCUMENTS

| | | | |
|---|---|---|---|
| 2018/0271616 A1 | 9/2018 | Schuh et al. | |
| 2018/0279993 A1 | 10/2018 | Crawford et al. | |
| 2018/0280097 A1 | 10/2018 | Cooper et al. | |
| 2018/0296283 A1 | 10/2018 | Crawford et al. | |
| 2018/0311001 A1 | 11/2018 | Prisco | |
| 2018/0316139 A1 | 11/2018 | Berrocal et al. | |
| 2018/0318018 A9 | 11/2018 | Johnson et al. | |
| 2018/0325609 A1 | 11/2018 | Kostrzewski et al. | |
| 2018/0325610 A1 | 11/2018 | Cameron et al. | |
| 2018/0333213 A1 | 11/2018 | Johnson et al. | |
| 2019/0000561 A1 | 1/2019 | Decker et al. | |
| 2019/0000569 A1 | 1/2019 | Crawford et al. | |
| 2019/0000571 A1 | 1/2019 | Johnson et al. | |
| 2019/0009416 A1 | 1/2019 | Kalb et al. | |
| 2019/0029765 A1 | 1/2019 | Crawford et al. | |
| 2019/0038366 A1 | 2/2019 | Johnson et al. | |
| 2019/0046281 A1 | 2/2019 | Johnson et al. | |
| 2019/0105116 A1 | 4/2019 | Johnson et al. | |
| 2019/0117313 A1 | 4/2019 | Crawford | |
| 2019/0133666 A1 | 5/2019 | Johnson et al. | |
| 2019/0150901 A1 | 5/2019 | Ponzer et al. | |
| 2019/0167365 A1 | 6/2019 | Chaplin et al. | |
| 2019/0216554 A1 | 7/2019 | Kapadia | |
| 2019/0223966 A1 | 7/2019 | Holop et al. | |
| 2019/0231448 A1 | 8/2019 | McBrien et al. | |
| 2019/0231455 A1 | 8/2019 | Cooper et al. | |
| 2019/0231464 A1 | 8/2019 | Wixey et al. | |
| 2019/0239964 A1 | 8/2019 | LeBoeuf, II et al. | |
| 2019/0254763 A1 | 8/2019 | Lambrecht et al. | |
| 2019/0269467 A1 | 9/2019 | Forsyth et al. | |
| 2019/0269471 A1 | 9/2019 | Phoolchund et al. | |
| 2019/0274765 A1 | 9/2019 | Crawford et al. | |
| 2019/0274766 A1 | 9/2019 | Holop et al. | |
| 2019/0282315 A1 | 9/2019 | Loh et al. | |
| 2019/0298461 A1 | 10/2019 | Holop et al. | |
| 2019/0298471 A1 | 10/2019 | Holop | |
| 2019/0380794 A1 | 12/2019 | Al Jewad et al. | |
| 2019/0388161 A1 | 12/2019 | Cicchini et al. | |
| 2020/0015857 A1 | 1/2020 | Rout et al. | |
| 2020/0015858 A1 | 1/2020 | Paster et al. | |
| 2020/0046394 A1 | 2/2020 | Cau | |
| 2020/0061847 A1 | 2/2020 | Dixon | |
| 2020/0069385 A1 * | 3/2020 | Ago | A61B 46/10 |
| 2020/0170724 A1 | 6/2020 | Flatt et al. | |
| 2020/0170740 A1 | 6/2020 | Galili et al. | |
| 2020/0323521 A1 | 10/2020 | Wehrli et al. | |

FOREIGN PATENT DOCUMENTS

| | | |
|---|---|---|
| JP | 6321852 B1 | 5/2018 |
| WO | 2011037394 A2 | 3/2011 |

OTHER PUBLICATIONS

English language abstract for WO 2011/037394 A1 extracted from espacenet.com database on Feb. 2, 2023, 1 page.

* cited by examiner

QUICK-CONNECT MOUNTING SYSTEM FOR SURGICAL COMPONENTS

CROSS-REFERENCE TO RELATED APPLICATIONS

The present application claims priority to and all the benefits of U.S. Provisional Patent Application No. 63/305,781 filed on Feb. 2, 2022, the contents of which are hereby incorporated by reference in their entirety.

BACKGROUND

For certain surgical systems, there is often a need to mount different components together to one another to promote accuracy and predictability of the position of the components relative to one another. One example of such a system is a robotic system, which is used to perform surgical procedures and typically includes a robotic arm and an end effector and/or tool that need to be coupled to the robotic arm. In some conventional systems, the end effector is coupled to the robotic arm using a sequence of multiple steps that require excessive installation time or that require the assistance of multiple individuals. The same problems occur when uncoupling the two components. For example, one conventional system requires installation of one or more fasteners to rigidly secure the end effector to the robotic arm. While the fasteners do permit coupling, they often require supplemental tools for attaching and detaching the end effector from the robotic arm. The requirement of installation tools further introduces inefficiency in securing the mounting components to one another.

As such, there is a need in the art for a mounting system that address at least the aforementioned problems.

SUMMARY

This Summary introduces a selection of concepts in a simplified form that are further described in the Detailed Description below. This Summary is not intended to limit the scope of the claimed subject matter and does not necessarily identify each and every key or essential feature of the claimed subject matter.

According to a first aspect, a mounting system is provided. The mounting system includes a first mounting portion. The first mounting portion has a first body. A lip extends from the first body. A push pin extends from the first body and is spaced from the lip. The mounting system also includes a second mounting portion. The second mounting portion is configured to be coupled with the first mounting portion. The second mounting portion has a second body extending along an axis. The second body has an outer surface and an inner surface. The inner surface defines a bore that extends along the axis. The second body defines a plurality of openings through the inner and outer surfaces. Each retainer of a plurality of retainers is moveable within one of the openings relative to the second body in a direction perpendicular to the axis. A loading assembly is disposed within the bore of the second body. The loading assembly is moveable along the axis to a first state in response to the push pin interfacing the loading assembly when the first mounting portion is coupled to the second mounting portion. In the first state, the loading assembly is configured to move the plurality of retainers to a coupling position. In the coupling position, each retainer extends through one of the openings beyond the outer surface of the second body. Each retainer extends beyond the outer surface of the second body to abut the lip of the first mounting portion in the coupling position to secure the first mounting portion to the second mounting portion.

According to a second aspect, a mounting portion is provided for facilitating coupling in a surgical system, the mounting portion comprising: a body extending along an axis, the body having an outer surface and an inner surface, the inner surface defining a bore that extends along the axis, and the body defining a plurality of openings through the inner and outer surfaces; a plurality of retainers, each retainer sized to fit within one of the openings; and a loading assembly disposed within the bore of the body, the loading assembly having a loading shaft sized to fit within the bore of the body.

According to a third aspect, a mounting portion is provided for facilitating coupling in a surgical system, the mounting portion comprising: a body; a lip extending from the body; and a push pin extending from the body and spaced from the lip; wherein the body and the lip collectively define a cavity.

According to a fourth aspect, a method is provided of coupling a first mounting portion with a second mounting portion, wherein the first mounting portion includes a push pin, a first body, and a lip extending from the first body, and wherein the second mounting portion includes a second body, a plurality of retainers, and a loading assembly to unlock the loading assembly, the method comprising the steps of: moving a push rod of the loading assembly within a loading shaft of the loading assembly; moving the loading shaft along an axis to abut the retainers; moving the plurality of retainers through openings in the second body to a coupling position; and abutting the lip of the first mounting portion with the plurality of retainers to secure the first mounting portion to the second mounting portion.

According to a fifth aspect, a mounting system is provided. The mounting system includes a first mounting portion. The first mounting portion has a first body. A lip extends from the first body. A push pin extends from the first body and is spaced from the lip. The mounting system also includes a second mounting portion. The second mounting portion is configured to be coupled with the first mounting portion. The second mounting portion has a second body. The second body has an outer surface and an inner surface. The inner surface defines a bore. The second body supports a plurality of retainers that are moveable relative to the second body. A loading assembly is disposed within the bore of the second body. The loading assembly is moveable within the bore to a first state in response to the push pin interfacing the loading assembly when the first mounting portion is coupled to the second mounting portion. In the first state, the loading assembly is configured to move the plurality of retainers to a coupling position. In the coupling position, one or more of the retainers extend beyond the outer surface of the second body to abut the lip of the first mounting portion in the coupling position to secure the first mounting portion to the second mounting portion.

Any of the aspects above can be combined in part, or in whole.

Any of the aspects above can be combined, in part, or in whole, with any of the following implementations:

In one implementation, the loading assembly is moveable along the axis to a second state, and wherein the loading assembly in the second state permits the plurality of retainers to move to a decoupling position whereby the first mounting portion is permitted to separate from the second mounting portion. In one implementation, the bore is straight. In another implementation, the bore is angled, curved, or irregularly shaped.

In one implementation, each retainer in the coupling position extends through one of the openings beyond the outer surface of the second body. In one implementation, each retainer in the decoupling position is closer to the axis than in the coupling position. In one implementation, the plurality of retainers in the decoupling position are disposed within the bore and no part of each retainer projects outwardly beyond the outer surface of the second body. In one implementation, each retainer in the coupling position extends through one of the openings beyond the inner surface of the second body. In one implementation, each retainer in the decoupling position is farther away from the axis than in the coupling position. In one implementation, the plurality of retainers in the decoupling position are disposed outside of the bore and no part of each retainer projects inwardly of the inner surface of the second body. In one implementation, the loading assembly comprises a loading shaft disposed within the bore of the second body. In one implementation, the loading shaft is moveable along the axis to a first load position in the first state of the loading assembly where the loading shaft abuts the plurality of retainers to move the plurality of retainers to the coupling position. In one implementation, the loading shaft is moveable along the axis to a second load position in the second state of the loading assembly where the loading shaft permits each retainer to move to the decoupling position.

In one implementation, the loading assembly comprises a stopper and a push rod. In one implementation, the push rod being moveable along the axis. In one implementation, the push rod defines a recess configured to receive the stopper. In one implementation, the stopper and the push rod are configured to permit the loading shaft to move relative to the second body when the push rod receives the stopper in the recess.

In one implementation, the loading shaft defines a channel extending along the axis. In one implementation, the push rod is moveable along the axis within the channel. In one implementation, the push rod is sized to fit within the channel. In one implementation, the loading shaft defines an aperture configured to receive the stopper. In one implementation, the second body defines a groove configured to receive the stopper. In one implementation, the push rod is moveable along the axis relative to the loading shaft to a locked position where the stopper is received in the aperture of the loading shaft and in the groove of the second body to retain the loading shaft in the second load position. In one implementation, the push rod is moveable along the axis relative to the loading shaft to an unlocked position where the stopper is received in the aperture of the loading shaft and in the recess of the push rod to permit the loading shaft to move relative to the second body. In one implementation, the push rod is in the locked position in the second state of the loading assembly. In one implementation, the push rod is in the unlocked position in the first state of the loading assembly. In one implementation, the push pin interfaces the push rod to move the push rod from the locked position to the unlocked position. In one implementation, the loading assembly further comprises a push rod biasing member configured to bias the push rod to the locked position.

In one implementation, the second body defines a slot extending about and along the axis. In one implementation, the loading assembly comprises a pin being attached to the loading shaft and extending through the bore and the loading shaft. In one implementation, the pin is received by the slot to limit range of motion of the loading shaft relative to the second body.

In one implementation, the second mounting portion comprises a release assembly coupled to the loading shaft of the loading assembly. In one implementation, the release assembly is configured to move the loading shaft from the first load position to the second load position to permit the first mounting portion to separate from the second mounting portion. In one implementation, the release assembly comprises a head being attached to the loading shaft. In one implementation, the head is configured to be grasped by a user to move the loading shaft from the first load position to the second load position. In one implementation, the release assembly comprises a locking tab rotatably coupled to the head. In one implementation, the locking tab is moveable to a first locking tab position where the locking tab abuts the second body to prevent movement of the loading shaft relative to the second body. In one implementation, the locking tab is moveable to a second locking tab position different from the first locking tab position where movement of the loading shaft relative to the second body is permitted. In one implementation, the release assembly comprises a locking tab biasing member to bias the locking tab to the first locking tab position.

In one implementation, the loading assembly comprises a loading shaft biasing member to bias the loading shaft to the first load position.

In one implementation, the plurality of openings are defined about the axis. In one implementation, the one or more of the plurality of openings are sized to prevent movement of one or more of the plurality of retainers to pass through the one or more of the openings.

In one implementation, one or more of the plurality of retainers moves relative to the second body in a direction radial to the axis. In one implementation, each retainer of the plurality of retainers is disposed radially inward of the lip to permit separation of the first mounting portion from the second mounting portion. In one implementation, the one or more of the plurality of retainers comprises a spherical shape.

In one implementation, the first body and the lip collectively define a cavity. In one implementation, the push pin is disposed within the cavity.

In one implementation, a plurality of kinematic couplers are coupled to one of the first and second mounting portions. In one implementation, the kinematic couplers are configured to engage the other of the first and second mounting portions to provide a kinematic coupling between the first and second mounting portions. In one implementation, the kinematic couplers constrain six degrees of freedom of movement between the first and second mounting portions. In one implementation, the plurality of retainers of the second mounting portion abut the lip of the first mounting portion.

In one implementation, the first mounting portion is coupled to a first surgical or medical component. In one implementation, the second mounting portion is coupled to a second surgical or medical component. In one implementation, either the first or second mounting portion is coupled to a non-surgical component and the other mounting portion is coupled to a surgical or medical component. In one implementation, both the first and second mounting portions are coupled to a non-surgical component. In one implementation, the first and/or second surgical component are any one or more of: a surgical navigation tracker, a surgical guide component, a powered surgical instrument component, a surgical hand tool component, a surgical robot component, a robotic link or joint, a robot link interface, a surgical cart, a sterile interface plate, an end effector, a passive arm component, a surgical table component, a limb holder, an imaging device, a localizer, a surgical monitor, or the like.

Any of the implementations above can be combined in part, or in whole.

DETAILED DESCRIPTION

I. Overview of Example Systems Usable with Mounting System

Figure 1:
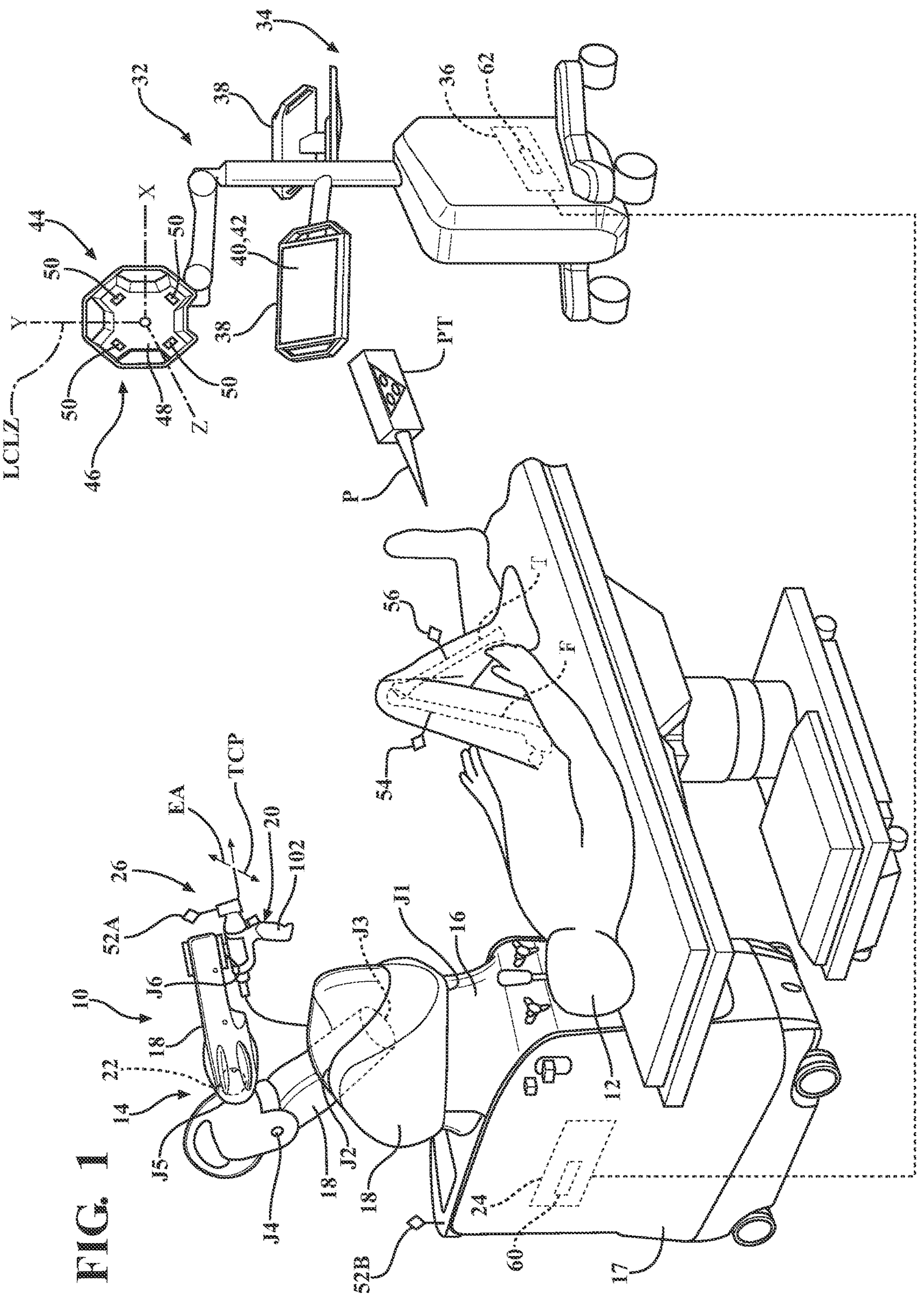
FIG. 1 is a perspective view of a robotic system for manipulating a target tissue of a patient with a tool, according to one implementation.

Referring to FIG. 1, in one non-limiting implementation, a robotic system 10 is illustrated. The example robotic system 10 is a surgical robotic system. However, the mounting system described herein may be implemented with non-surgical systems or components. The system 10 is useful for treating a surgical site or anatomical volume of a patient 12, such as treating bone or soft tissue. In FIG. 1, the patient 12 is undergoing a surgical procedure. The surgical procedure may involve tissue removal or other forms of treatment. Treatment may include cutting, coagulating, lesioning the tissue, other in-situ tissue treatments, or the like. In some examples, the surgical procedure involves shoulder replacement surgery, partial or total knee or hip replacement surgery, spine surgery, or ankle surgery. In some examples, the system 10 is designed to cut away material to be replaced by surgical implants, such as shoulder implants, partial or total knee implants, hip implants, spine implants, or ankle implants. As shown in FIG. 1, the system 10 may treat an anatomy (surgical site) of a patient 12, such as bone or soft tissue. In FIG. 1, the patient 12 is undergoing a surgical procedure. The anatomy in FIG. 1 includes a femur (F) and a tibia (T) of the patient 12. The surgical procedure may involve tissue removal or treatment. Treatment may include cutting, coagulating, lesioning the tissue, treatment in place of tissue, or the like. In some examples, the surgical procedure involves partial or total knee or hip replacement surgery. In one example, the system 10 is designed to cut away material to be replaced by surgical implants, such as hip and knee implants, including unicompartmental, bicompartmental, multicompartmental, or total knee implants. Some of these types of implants are shown in U.S. Pat. No. 9,937,058, entitled, "Prosthetic Implant and Method of Implantation," the disclosure of which is hereby incorporated by reference. The system 10 and method disclosed herein may be used to perform other procedures, surgical or non-surgical, or may be used in industrial applications or other applications where robotic systems are utilized.

The system 10 includes a manipulator 14. The manipulator 14 has a base 16 and plurality of links 18. A manipulator cart 20 can support the manipulator 14 such that the manipulator 14 is fixed to the manipulator cart 20. In other examples, the manipulator 14 can be mounted to a surgical patient table. The links 18 collectively form one or more arms or linkages of the manipulator 14 with adjacent links being connected by joints. The manipulator 14 may have a serial, robotic arm configuration (as shown in FIG. 1), a parallel, robotic arm configuration, or any other suitable manipulator configuration. In other examples, more than one manipulator 14 may be utilized in a multiple arm configuration.

In the example shown in FIG. 1, the manipulator 14 comprises a plurality of joints J1-J6 and a plurality of joint encoders 22 located at the joints J1-J6 for determining position data (e.g., rotation angles) of the joints J1-J6. For simplicity, only one joint encoder 22 is illustrated in FIG. 1, although other joint encoders 22 may be similarly illustrated. The manipulator 14 according to one example has six joints J1-J6 implementing six-degrees of freedom (DOF) for the manipulator 14. However, the manipulator 14 may have any number of degrees of freedom and may have any suitable number of joints J and may have redundant joints.

The manipulator 14 need not require joint encoders 22 but may alternatively, or additionally, utilize motor encoders present on motors at each joint J. Also, the manipulator 14 need not require rotary joints, but may alternatively, or additionally, utilize one or more prismatic joints. Any suitable combination of joint types is contemplated.

The base 16 of the manipulator 14 is generally a portion of the manipulator 14 that provides a fixed reference coordinate system for other components of the manipulator 14 or the system 10 in general. Generally, the origin of a manipulator coordinate system is defined at the fixed reference of the base 16. The base 16 may be defined with respect to any suitable portion of the manipulator 14, such as one or more of the links 18. Alternatively, or additionally, the base 16 may be defined with respect to the manipulator cart 20, such as where the manipulator 14 is physically attached to the cart 20. In one example, the base 16 is defined at an intersection of the axes of joints J1 and J2. Thus, although joints J1 and J2 are moving components in reality, the intersection of the axes of joints J1 and J2 is nevertheless a virtual fixed reference pose, which provides both a fixed position and orientation reference and which does not move relative to the manipulator 14 and/or manipulator cart 20.

In other examples, the manipulator 14 can be a hand-held manipulator where the base 16 is a base portion of a tool (e.g., a portion held free-hand by the user) and the tool tip is movable relative to the base portion. The base portion has a reference coordinate system that is tracked and the tool tip has a tool tip coordinate system that is tracked relative to the reference coordinate system. In some instances, the hand-held manipulator can be mounted to a robotic arm of the system 10 or to any other passive or active linkage assembly that may be mounted to the surgical table and/or to the patient 12.

The manipulator 14 and/or manipulator cart 20 house a manipulator controller 24, or other type of control unit. The manipulator controller 24 may comprise one or more computers, or any other suitable form of controller that directs the motion of the manipulator 14. The manipulator controller 24 may have a central processing unit (CPU) and/or other processors, memory (not shown), and storage (not shown). The manipulator controller 24 is loaded with software as described below. The processors could include one or more processors to control operation of the manipulator 14. The processors can be any type of microprocessor, multi-processor, and/or multi-core processing system. The manipulator controller 24 may additionally, or alternatively, comprise one or more microcontrollers, field programmable gate arrays, systems on a chip, discrete circuitry, and/or other suitable hardware, software, or firmware that is capable of carrying out the functions described herein. The term processor is not intended to limit any configuration to a single processor. The manipulator 14 may also comprise a user interface with one or more displays and/or input devices (e.g., push buttons, keyboard, mouse, microphone (voice-activation), gesture control devices, touchscreens, etc.).

A surgical tool 26 couples to the manipulator 14 and is movable relative to the base 16 to interact with the anatomy. The tool 26 is or forms part of an end effector supported by the manipulator 14 in certain configurations. The tool 26 may be grasped by the user. One possible arrangement of the manipulator 14 and the tool 26 is described in U.S. Pat. No. 9,119,655, entitled, "Surgical Manipulator Capable Of Controlling A Surgical Tool In Multiple Modes," filed on Aug. 2, 2013, the disclosure of which is hereby incorporated herein by reference. The manipulator 14 and the tool 26 may be arranged in alternative configurations. The tool 26 can be like that shown in U.S. Pat. No. 9,566,121, entitled, "End Effector Of A Surgical Robotic Manipulator," filed on Mar. 15, 2014, hereby incorporated herein by reference.

The tool 26 includes an energy applicator EA designed to contact and remove the tissue of the patient 12 at the surgical site. In one example, the energy applicator EA is a saw blade. Alternatively, the energy applicator EA may be a drill bit, a bur, an ultrasonic vibrating tip, or the like. In other examples, the tool 26 can be a laser cutter, a machine vision camera, an ultrasound scanner, an arthroscope, or the like. In some versions, the tool 26 includes non-motorized accessories such as a probe, a retractor, a cutting guide, or the like. The tool 26 and/or energy applicator EA/accessory may comprise any geometric feature, e.g., perimeter, circumference, radius, diameter, width, length, volume, area, surface/plane, range of motion envelope (along any one or more axes), etc. The geometric feature may be considered to determine how to locate the tool 26 relative to the tissue at the surgical site to perform the desired treatment. In the version shown, the tool 26 comprises a tool driver **26*a* (see FIG. 2) that houses any driving motor for the energy applicator EA, e.g., to drive saw blade oscillation, burr rotation, drill rotation, etc. The tool 26 also comprises a tool holder 26*b* that releasably connects to the tool driver 26*a* to interchange different energy applicators EA. The tool holder 26*b* releasably holds the energy applicator EA. The tool holder 26*b* can be releasably connected to the tool driver 26*a*** using any suitable type of connection, e.g. snap-fit connection, bayonet-type connection, fasteners, collet connections, or the like.

The tool 26 may comprise a tool controller 28 to control operation of the tool 26, such as to control power to the tool (e.g., to a rotary, driving motor of the tool 26), control movement of the tool 26, control irrigation/aspiration of the tool 26, and/or the like. The tool controller 28 may be in communication with the manipulator controller 24 or other components. The tool 26 may also comprise a user interface UI with one or more displays and/or input devices (e.g., push buttons, keyboard, mouse, microphone (voice-activation), gesture control devices, touchscreens, etc.). The manipulator controller 24 controls a state (e.g., position and/or orientation) of the tool 26 (e.g., the TCP) with respect to a coordinate system, such as the manipulator coordinate system. The manipulator controller 24 can control (linear or angular) velocity, acceleration, or other derivatives of motion of the tool 26.

The tool center point (TCP), in one example, is a predetermined reference point or coordinate system defined at the energy applicator EA. The TCP has a known, or able to be calculated (i.e., not necessarily static), pose relative to other coordinate systems. The geometry of the energy applicator EA is known in or defined relative to a TCP coordinate system. The TCP may be located at the spherical center of the burr of the tool 26 such that only one point is tracked. The TCP may be defined in various ways depending on the configuration of the energy applicator EA. The manipulator 14 could employ the joint/motor encoders, or any other non-encoder position sensing method, to enable a pose of the TCP to be determined. The manipulator 14 may use joint measurements to determine TCP pose and/or could employ techniques to measure TCP pose directly. The control of the tool 26 is not limited to a center point. For example, any suitable primitives, meshes, etc., can be used to represent the tool 26.

The system 10 may further include a navigation system 32. One example of the navigation system 32 is described in U.S. Pat. No. 9,008,757, filed on Sep. 24, 2013, entitled, "Navigation System Including Optical And Non-Optical Sensors," hereby incorporated herein by reference. The navigation system 32 tracks movement of various objects. Such objects include, for example, the manipulator 14, the tool 26 and the anatomy, e.g., the femur F and tibula T. The navigation system 32 tracks these objects to gather state information of each object with respect to a (navigation) localizer coordinate system. Coordinates in the localizer coordinate system may be transformed to the manipulator coordinate system, and/or vice-versa, using transformations.

The navigation system 32 includes a cart assembly 34 that houses a navigation controller 36, and/or other types of control units. A navigation user interface UI is in operative communication with the navigation controller 36. The navigation user interface includes one or more displays 38. The navigation system 32 is capable of displaying a graphical representation of the relative states of the tracked objects to the user using the one or more displays 38. The navigation user interface UI further comprises one or more input devices to input information into the navigation controller 36 or otherwise to select/control certain aspects of the navigation controller 36. Such input devices include interactive touchscreen displays. However, the input devices may include any one or more of push buttons, a keyboard, a mouse, a microphone (voice-activation), gesture control devices, and the like.

The navigation system 32 also includes a navigation localizer 44 coupled to the navigation controller 36. In one example, the localizer 44 is an optical localizer and includes a camera unit 46. The camera unit 46 has an outer casing 48 that houses one or more optical sensors 50. The localizer 44 may include its own localizer controller 52 and may further or alternatively include one or more video cameras VC. The localizer 44 can utilize any one or combination of the following tracking modalities: optical, electromagnetic, radio frequency, machine vision, and/or ultrasound tracking. These modalities may or may not require individual trackers.

In the implementation shown in FIG. 1, the navigation system 32 includes one or more trackers. In one example, the trackers include a pointer tracker PT, one or more tool or manipulator trackers 52A, 52B, a first patient tracker 54, and a second patient tracker 56. In the illustrated example of FIG. 1, one tool tracker 52A is fixed with respect to the tool 26, the first patient tracker 54 is firmly affixed to the femur F of the patient 12, and the second patient tracker 56 is firmly affixed to the tibia T of the patient 12. In this example, the patient trackers 54, 56 are firmly affixed to sections of bone. The pointer tracker PT is firmly affixed to a pointer used for registering the anatomy to the localizer coordinate system. The manipulator tracker 52B may be affixed to any suitable component of the manipulator 14, in addition to, or other than the tool 26, such as the base 16, the cart 20, or any one or more links 18 of the manipulator 14. The trackers 52A, 52B, 54, 56, PT may be fixed to their respective components in any suitable manner. For example, the trackers may be rigidly fixed, flexibly connected (optical fiber), or not physically connected at all (ultrasound), as long as there is a suitable (supplemental) way to determine the relationship (measurement) of that respective tracker to the object that it is associated with. In some cases, only one of the tool and manipulator trackers 52A, 52B are used, or both the tool and manipulator trackers 52A, 52B may be used.

In the illustrated configuration, the trackers 52A, 52B, 54, 56, PT are passive trackers. Accordingly, each tracker 52A, 52B, 54, 56, PT has at least three passive tracking elements or markers M, such as reflectors, for reflecting light from the localizer 44 back to the optical sensors 50. In other configurations, the trackers 52A, 52B, 54, 54, PT are active trackers and may have light emitting diodes or LEDs transmitting light, such as infrared light to the optical sensors 50. Based on the received optical signals, navigation controller 36 generates data indicating the relative positions and orientations of the trackers 52A, 52B, 54, 56, PT relative to the localizer 44 using conventional triangulation techniques. In some cases, more or fewer markers may be employed. For instance, in cases in which the object being tracked is rotatable about a line, two markers can be used to determine an orientation of the line by measuring positions of the markers at various locations about the line. It should be appreciated that the localizer 44 and trackers 52A, 52B, 54, 56, PT, although described above as utilizing optical tracking techniques, could alternatively, or additionally, utilize other tracking modalities to track the objects, such as electromagnetic tracking, radio frequency tracking, inertial tracking, ultrasound-based tracking, fiber-optic tracking, machine-vision tracking, combinations thereof, and the like.

The localizer 44 tracks the trackers 52A, 52B, 54, 56, PT to determine a state of each of the trackers 52A, 52B, 54, 56, PT, which correspond respectively to the state of the object respectively attached thereto. The localizer 44 provides the state of the trackers 52A, 52B, 54, 56, PT to the navigation controller 36. In one example, the navigation controller 36 determines and communicates the state of the trackers 52A, 52B, 54, 56, PT to the manipulator controller 24. As used herein, the state of an object includes, but is not limited to, data that defines the position and/or orientation of the tracked object or equivalents/derivatives of the position and/or orientation. For example, the state may be a pose of the object, and may include linear velocity data, and/or angular velocity data, and the like.

The navigation controller 36 may comprise one or more computers, or any other suitable form of controller. Navigation controller 36 has a central processing unit (CPU) and/or other processors, memory (not shown), and storage (not shown). The processors can be any type of processor, microprocessor or multi-processor system. The navigation controller 36 is loaded with software. The software, for example, converts the signals received from the localizer 44 into data representative of the position and orientation of the objects being tracked. The navigation controller 36 may additionally, or alternatively, comprise one or more microcontrollers, field programmable gate arrays, systems on a chip, discrete circuitry, and/or other suitable hardware, software, or firmware that is capable of carrying out the functions described herein. The term processor is not intended to limit any configuration to a single processor.

In operation, for certain surgical tasks, the user can manipulate (e.g., apply force to or cause movement of) the tool 26 to perform the surgical procedure on the patient, such as drilling, cutting, sawing, reaming, implant installation, and the like. As the user manipulates the tool 26, the navigation system 32 tracks the location of the tool 26 and/or the manipulator 14 and provides haptic feedback (e.g., force feedback) to the user to limit the user's ability to move (or cause movement of) the tool 26 beyond one or more predefined virtual boundaries that are registered (or mapped)

to the patient's anatomy, which results in highly accurate and repeatable drilling, cutting, sawing, reaming, and/or implant placement.

In some configurations, the manipulator 14 operates in a passive manner and provides haptic feedback when the surgeon attempts to move the tool 26 beyond the virtual boundary. The haptic feedback (e.g., a form of stereotactic feedback) is generated by one or more actuators (e.g., joint motors) of the manipulator 14 and transmitted to the user via a flexible transmission, such as a cable drive transmission. When the manipulator 14 is not providing haptic feedback, the manipulator 14 is freely moveable by the user. In some configurations, like that shown in U.S. Pat. No. 9,566,122, incorporated herein by reference, the manipulator 14 is manipulated by the user in a similar manner, but the manipulator 14 operates in an active manner. For instance, the user applies force to the tool 26, which is measured by a force/torque sensor S (see FIG. 17), and the manipulator 14 emulates the user's desired movement based on measurements from the force/torque sensor S. For other surgical tasks, the manipulator 14 may operate in an autonomous, semi-autonomous or automated manner.

Figure 17:
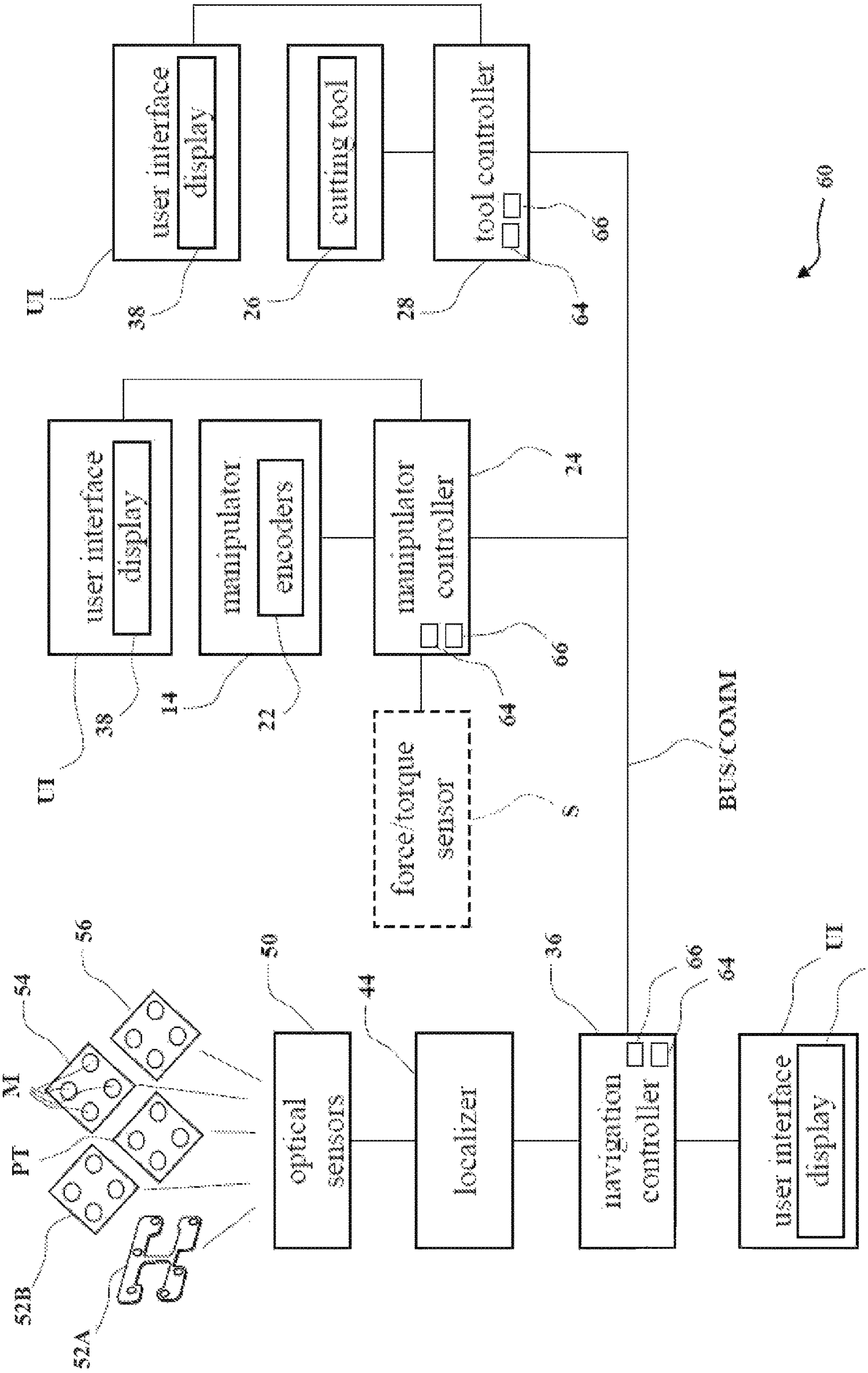
FIG. 17 is a block diagram of a control system for controlling the surgical system, according to one implementation.

Referring to FIG. 17, the system 10 includes a control system 60 that comprises, among other components, the manipulator controller 24, the navigation controller 36, and the tool controller 28. The control system 60 further includes one or more software programs and software modules. The software modules may be part of the program or programs that operate on the manipulator controller 24, navigation controller 36, tool controller 28, or any combination thereof, to process data to assist with control of the system 10. The software programs and/or modules include computer readable instructions stored in non-transitory memory 64 on the manipulator controller 24, navigation controller 36, tool controller 28, or a combination thereof, to be executed by one or more processors 66 of the controllers 24, 28, 36. The memory 64 may be any suitable configuration of memory, such as RAM, non-volatile memory, etc., and may be implemented locally or from a remote database. Additionally, software modules for prompting and/or communicating with the user may form part of the program or programs and may include instructions stored in memory 64 on the manipulator controller 24, navigation controller 36, tool controller 28, or any combination thereof. The user may interact with any of the input devices of the navigation user interface UI or other user interface UI to communicate with the software modules. The user interface software may run on a separate device from the manipulator controller 24, navigation controller 36, and/or tool controller 28.

The control system 60 may comprise any suitable configuration of input, output, and processing devices suitable for carrying out the functions and methods described herein. The control system 60 may comprise the manipulator controller 24, the navigation controller 36, or the tool controller 28, or any combination thereof, or may comprise only one of these controllers. These controllers may communicate wirelessly, via a bus as shown in FIG. 17, or otherwise. The control system 60 may also be referred to as a controller. The control system 60 may comprise one or more microcontrollers, field programmable gate arrays, systems on a chip, discrete circuitry, sensors, displays, user interfaces, indicators, and/or other suitable hardware, software, or firmware that is capable of carrying out the functions described herein.

The manipulator controller 24 and/or the navigation controller 36 track the state of the tool 26 relative to the anatomy and the virtual boundaries. In one example, the state of the TCP is measured relative to the virtual boundaries for purposes of determining haptic forces to be applied to a virtual rigid body model via a virtual simulation so that the tool 26 remains in a desired positional relationship to the virtual boundaries (e.g., not moved beyond them, kept within them, etc.). The results of the virtual simulation are commanded to the manipulator 14.

In some configurations, using the navigation system 32, the pose of the tool 26 can be determined by tracking the location of the base 16 and the associated manipulator coordinate system via the manipulator tracker 52B and calculating the pose of the tool 26 based on joint encoder data from the joint encoders 22 (and/or motor encoders) at the joints J1-J6 (using kinematic data) and based on a known geometric relationship between the tool 26 and the manipulator 14. Ultimately, the localizer 44 and the trackers 52A, 52B, 54, 56, PT enable the determination of the pose of the tool 26 and the patient's anatomy so the navigation system 32 knows the relative relationship between the tool 26 and the patient's anatomy. However, in some cases, the manipulator tracker 52B may be out of view of the localizer 44, or the manipulator tracker 52B may not be used. Line-of-sight between one or more of the sensors 50 and the manipulator tracker 52B may be obstructed such that movement of the tool 26 cannot be reliably tracked solely using the manipulator tracker 52B and encoder data. In this case, the tool tracker 52A can be employed to track movement of the tool 26, i.e., the tool tracker 52A is detected by the localizer 44 to determine a pose of the tool 26 (e.g., of the TCP coordinate system of the tool 26).

II. Mounting System Configuration

Figure 2:
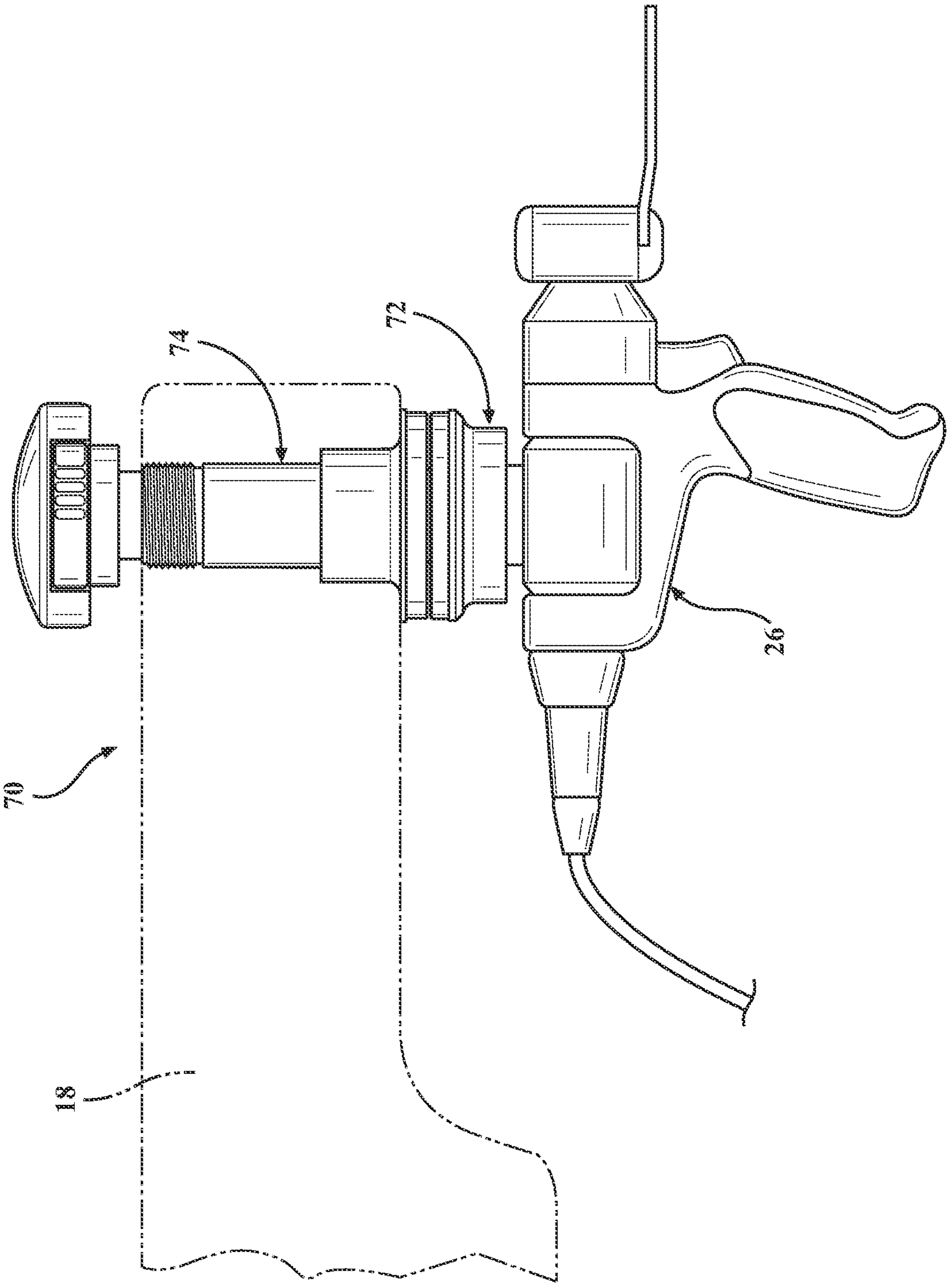
FIG. 2 is a side elevation view of a mounting system securing an end effector of the robotic system to a robotic arm of the robotic system, according to one implementation.

As shown in one non-limiting example of FIGS. 1 and 2, a mounting system 70 may be utilized for the surgical system 10. In the configuration illustrated in FIG. 1, the mounting system 70 may be used to mount the tool 26 to the manipulator 14. The mounting system 70 includes a first mounting portion 72 and a second mounting portion 74 configured to be coupled with the first mounting portion 72. In FIG. 1, the first mounting portion 72 is attachable or fixed to the tool 26 and the second mounting portion 74 is attachable or fixed to a distal portion of arm of the manipulator 14. In such a configuration, the tool 26 may be removably mounted to the manipulator 14 via coupling and decoupling of the first mounting portion 72 to the second mounting portion 74. In other configurations, the first mounting portion 72 may be secured or fixed to one of the links 18 of the manipulator 14 and the second mounting portion 74 may be secured or fixed to the tool 26.

Although an implementation of using the mounting system 70 with a robotic system has been described above, it is contemplated that each of the first and second mounting portions 72, 74 may be attached to any suitable surgical components of any surgical system. For instance, the first mounting portion 72 may be coupled to any first surgical component and the second mounting portion 74 may be coupled to any second surgical component.

The first and/or second surgical component may include, but not limited to, any one of a surgical navigation tracker, a surgical guide component, a powered surgical instrument component, a surgical hand tool component, a surgical robot component, a robotic link, a robotic joint, a robot link interface, a surgical cart, a sterile interface plate, an end effector, a passive adjustable (locking) arm component, a surgical table component, a limb holder, an imaging device, a localizer, a surgical monitor, or the like. Therefore, although the description below refers to using the mounting system 70 with the tool 26 and the robotic system 10, this implementation is for illustrative purposes and does not limit the spirit of the invention exclusively to this implementation.

Additionally, the first mounting portion 72 may be coupled to non-surgical components, including but not limited to components of any one or more of the following examples: non-surgical tools, non-surgical equipment, non-surgical robots, cameras, stands, monitors, adjustable arms, docking stations, and the like.

Furthermore, any description herein regarding what components or features are provided on the first mounting portion 72 or second mounting portion 74 may be interchangeable. In other words, the first and second mounting portions 72, 74 may be swapped with respect to what features they include or with respect to which component these mounting portions couple.

As shown in FIGS. 4, 6, and 12-15, the first mounting portion 72 has a first body 76 that is secured to the tool 26. The first mounting portion 72 includes a lip 78 extending from the first body 76. The first body 76 and the lip 78 may collectively form a "cup" that defines a cavity 80 for receiving the second mounting portion 74 as described in greater detail further below. The lip 78 may have a surface facing the cavity having a radius. The first mounting portion 72 further includes a push pin 82 extending from the first body 76. The push pin 82 is spaced from the lip 78. The push pin 82 can have various configurations. For example, the push pin 82 can be a static or an elastic component. The push pin 82 can be a cylinder, a cone, a semi-sphere, a triangular prism, or any other type of geometric shape to enable the push pin 82 to project from the first body 76. The push pin 82 can have any dimension (e.g., height or volume) suitable for the described examples. A distal part of the push pin 82 can be shaped in any suitable way, e.g., a flat end, a blunt end, a probe end, a sharp end, a dull end, a convex or concave end, a hollow end, a rounded end, or the like. The push pin 82 may be disposed within the cavity 80 defined by the lip 78 and the first body 76 such that the lip 78 at least partially surrounds the push pin 82. The lip 78 may surround the push pin 82 curl in toward the push pin 82. In some configurations, the push pin 82 extends farther from the first body 76 than the lip 78 extends from the first body 76. In other configurations, the lip 78 extends farther from the first body 76 than the push pin 82. In still other configurations, the push pin 82 and the lip 78 extend the same distance from the first body 76.

As shown in FIGS. 2, 3, 5, and 12-15, the second mounting portion 74 has a second body 84 extending along an axis A. The second body 84 has an outer surface and an inner surface. The inner surface defines a bore 86 that may extend along the axis A. The second body 84 defines a plurality of openings 88 through the inner and outer surfaces adjacent a proximal end of the second body 84 that is configured to be coupled to the first mounting portion 72. The openings 88 may be disposed about the axis A such that the openings 88 surround the bore 86.

The second mounting portion 74 includes a plurality of retainers 90 that may be at least partially disposed within the bore 86. In many configurations, one or more of the retainers 90 comprises a spherical body. It is contemplated that the retainers 90 may comprise other shapes or include features capable of engaging the lip 78 of the first mounting portion 72 to couple the first mounting portion 72 to the second mounting portion 74. For instance, one or more of the retainers 90 may comprise a conical or cylindrical configuration. In other examples, the one or more of the retainers 90 may comprise a cam pivotably coupled to the second body 84 and moveable relative to the second body 84 to secure the first mounting portion 72 to the second mounting portion 74. In another example, one or more of the retainers 90 may comprise a latch, catch, or hook pivotably coupled to the second body 84 and moveable within relative to the second body 84 to secure the first mounting portion 72 to the second mounting portion 74. Each retainer 90 is moveable within one of the openings 88 relative to the second body 84 in a direction perpendicular to the axis A. In many configurations, each retainer 90 is moveable within one of the openings 88 relative to the second body 84 in a radial direction to the axis A. One or more of the openings 88 may be sized to prevent movement of one or more of the retainers 90 to pass through the opening 88. In other words, one or more of the openings 88 may be sized large enough to permit a retainer 90 to extend radially outward beyond the outer surface of the second body 84, and small enough to prevent a retainer 90 from exiting the bore 86 through the opening 88.

Figure 12:
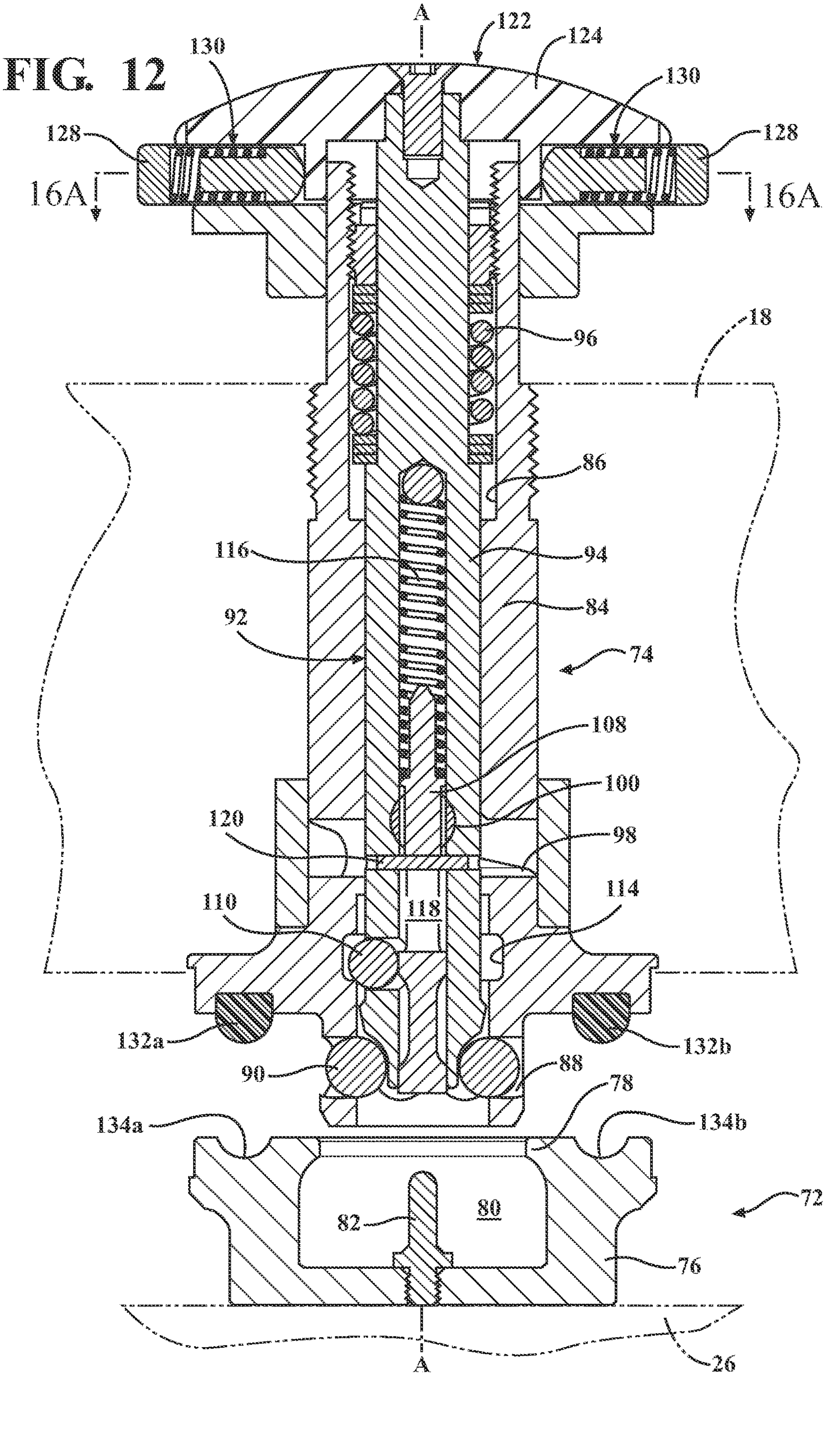
FIG. 12 is an elevational cross-section view of the mounting system in a first state, according to one implementation.
Figure 13:
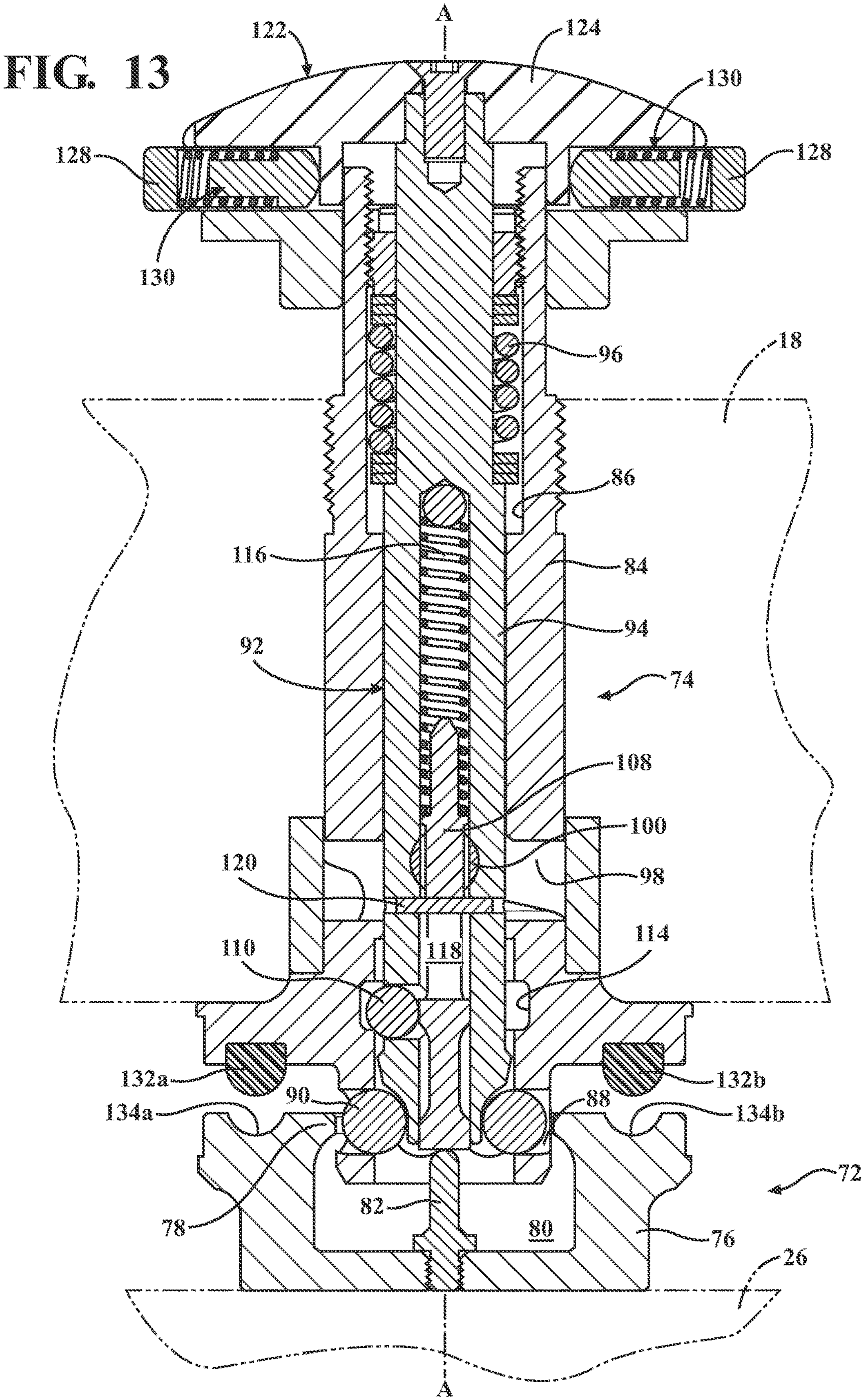
FIG. 13 is an elevational cross-section view of the mounting system in a second state, according to one implementation.

As shown in FIGS. 12-15, the second mounting portion 74 includes a loading assembly 92 disposed within the bore 86 of the second body 84. The loading assembly 92 is moveable along the axis A to a first state (FIG. 14) and often a second state (FIG. 12). In the first state, the first mounting portion 72 is secured to the second mounting portion 74. In the second state, the first mounting portion 72 may be separated from the second mounting portion 74. The loading assembly 92 is moveable in response to the push pin 82 interfacing the loading assembly 92 when the first mounting portion 72 is coupled to the second mounting portion 74. The loading assembly 92 is configured to move the retainers 90 to a coupling position in the first state. In some configurations of the coupling position, each retainer 90 extends through one of the openings 88 beyond the outer surface of the second body 84. Each retainer 90 may extend beyond the outer surface of the second body 84 to abut the lip 78 of the first mounting portion 72 in the coupling position to secure the first mounting portion 72 to the second mounting portion 74. The loading assembly 92 permits the retainers 90 to move to a decoupling position in the second state. In the decoupling position, each retainer 90 may be closer to the axis A than in the coupling position. In some configurations, the retainers 90 in the decoupling position may be disposed within the bore 86 and the opening 88 and no part of any retainer 90 projects outwardly beyond the outer surface of the second body 84. In other configurations, the retainers 90 are permitted to extend beyond the outer surface of the second body 84 less in the decoupling position than in the coupling position such that the retainers 90 do not abut the lip 78. In such a configuration, each retainer 90 in the decoupling position may project outwardly beyond the outer surface of the second body 84 and still be disposed radially inward of the lip 78 to permit separation of the first mounting portion 72 from the second mounting portion 74. Any one or more of the retainers 90 may have different radial positioning from one another in the decoupling position. For instance, some retainers 90 may be project beyond the outer surface of the second body 84, while other retainers 90 are located within the outer surface. Additionally, it is contemplated that those retainers 90 that extend beyond the outer surface may abut the lip 78, but the retainers 90 are able to move inward by the lip 78 during separation of the first mounting portion 72 from the second mounting portion 74.

The loading assembly 92 may include a loading shaft 94 disposed within the bore 86 of the second body 84. The loading shaft 94 may be moveable along the axis A to a first load position (see FIG. 14) in the first state of the loading assembly 92. In the first load position, the loading shaft 94 abuts the retainers 90 to move the retainers 90 to the coupling position. A proximal end of the loading shaft 94 may be tapered to assist in moving the retainers 90 outward in response to axial movement of the loading shaft 94. The proximal end may abut the retainers 90 to force the retainers 90 to the coupling position. The openings 88 of the second body 84 may be sized to prevent the retainers 90 from moving entirely out of the bore 86 of the second body 84 such that the retainers 90 in the coupling position still extend within the bore 86 far enough to prevent the loading shaft 94 from exiting the bore 86 of the second body 84 through the proximal end of the second body 84. The loading shaft 94 is moveable along the axis A to a second load position (see FIG. 12) in the second state of the loading assembly 92. In the second load position, the loading shaft 94 permits each retainer 90 to move to the decoupling position. The loading assembly 92 may have a loading shaft biasing member 96 to bias the loading shaft 94 to the first load position. The biasing member 96 can be any suitable biasing member, including, but not limited to: a compression spring, an extension spring, a coil spring, a helical spring, a leaf spring, a washer spring, a disc spring (e.g., Belleville disc spring), a piston (e.g., hydraulic, mechanical, or pneumatic), or the like.

Figure 5:
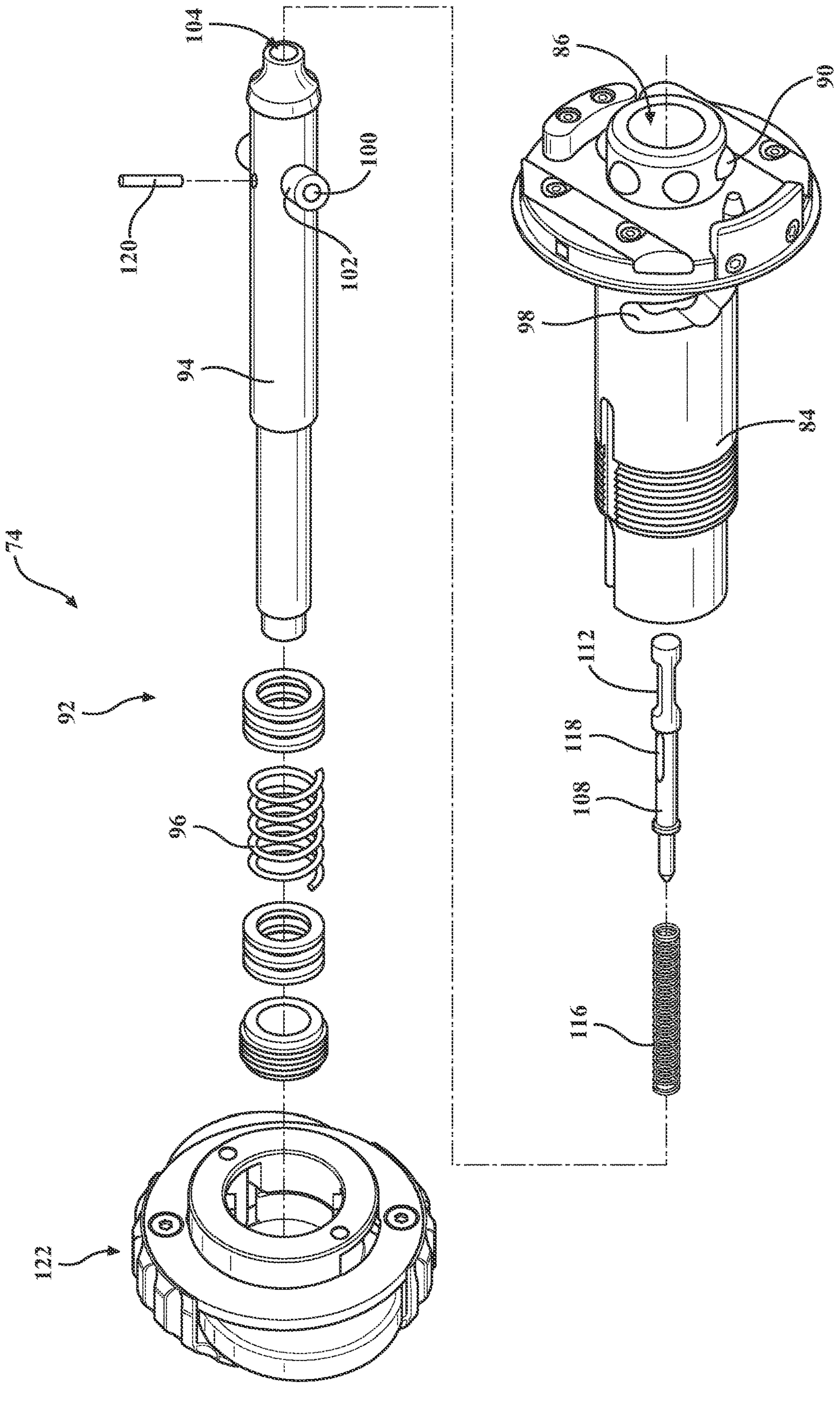
FIG. 5 is a partially exploded view of a portion of the mounting system, according to one implementation.
Figure 6:
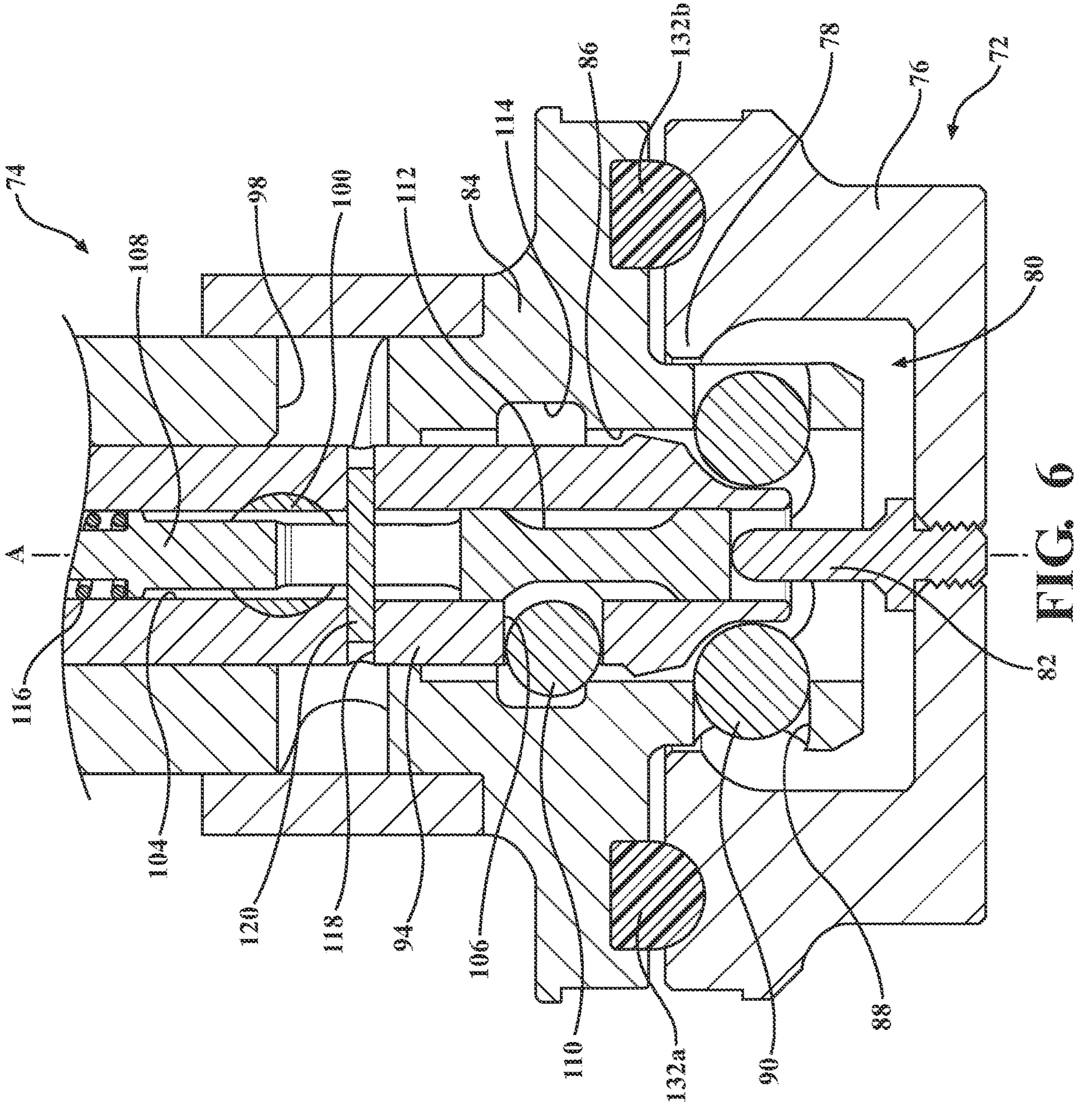
FIG. 6 is a partial sectional view of a first mounting portion being coupled to a second mounting portion, according to one implementation.
Figure 8:
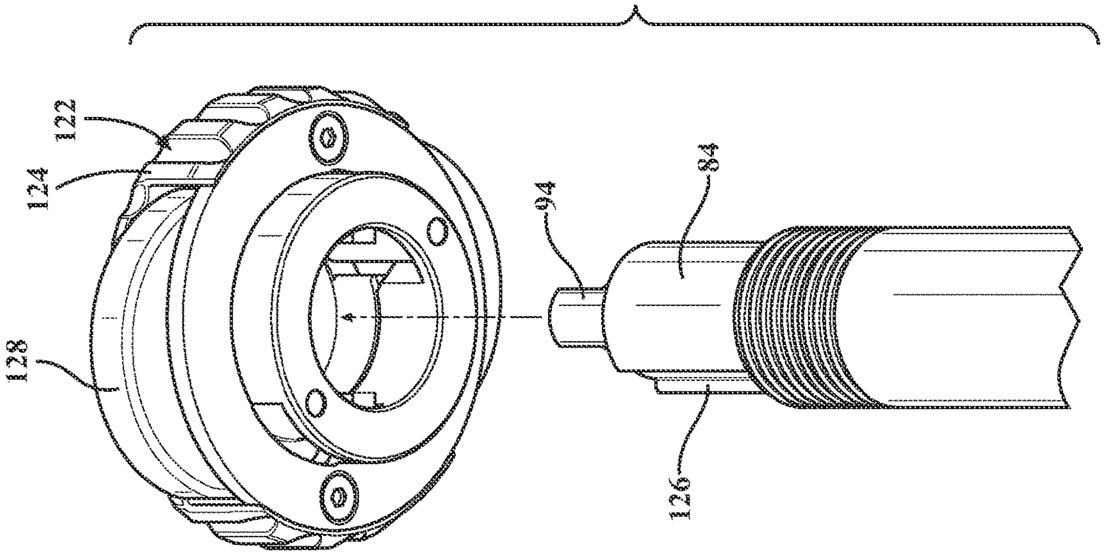
FIG. 8 is a partially exploded view of the second mounting portion including a release assembly, according to one implementation.
Figure 7:
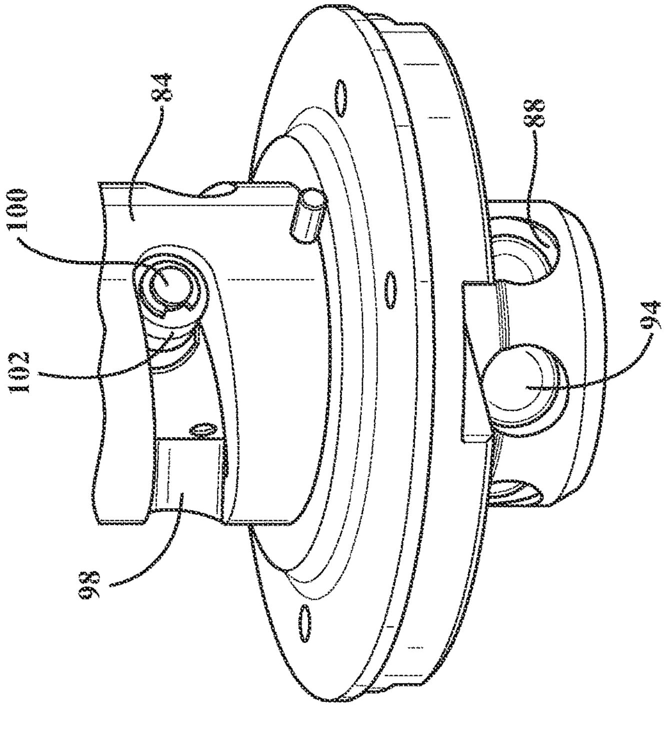
FIG. 7 is a partial perspective view of the second mounting portion, according to one implementation.
Figure 9:
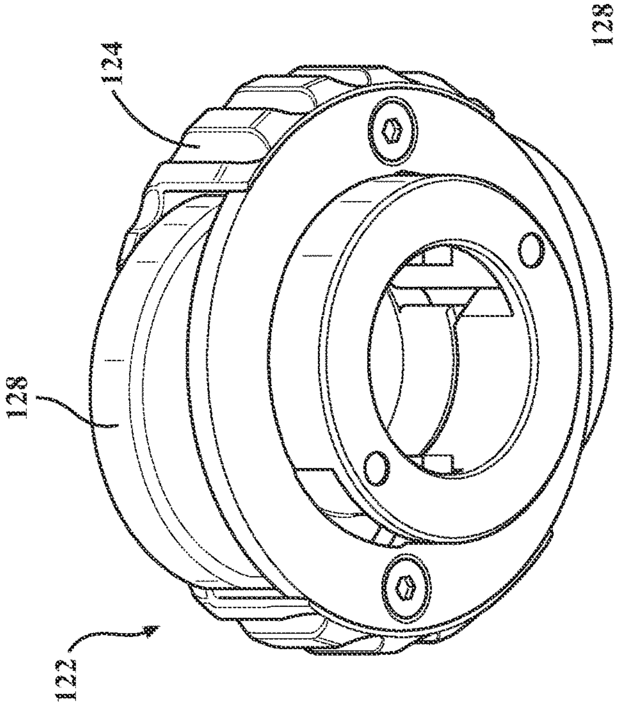
FIG. 9 is a perspective view of the release assembly, according to one implementation.
Figure 10:
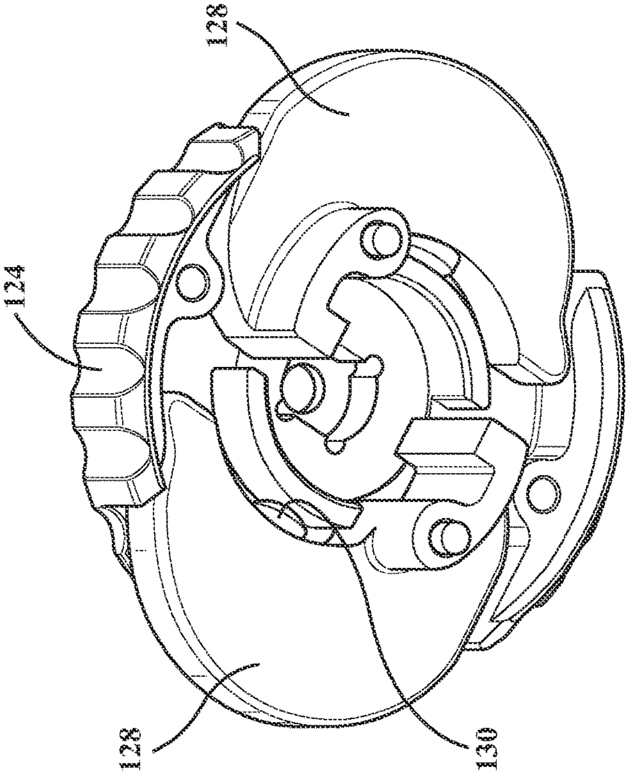
FIG. 10 is a partial perspective view of the release assembly, according to one implementation.
Figure 11:
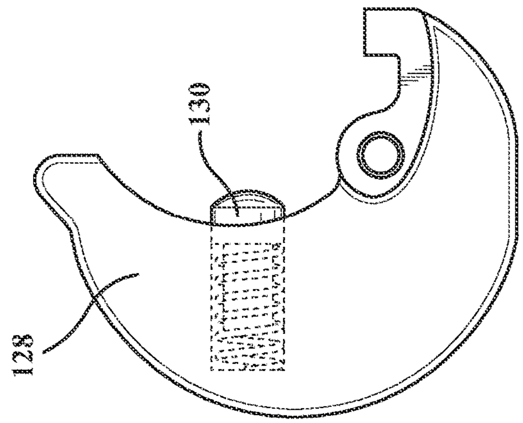
FIG. 11 is an elevation view, partially in phantom, of one locking tab of the release assembly, according to one implementation.

Referring to FIGS. 5 and 7, the second body 84 may define a slot 98 extending about and along the axis A. The slot 98 may have a curved, non-linear, spiral, or helical configuration. The slot 98 is defined on at least an inner surface of the second body 84 in fluid communication with the bore 86. In many configurations, the slot 98 extends through the inner and outer surface. The loading assembly 92 may include a loading shaft pin 100 being attached to the loading shaft 94 and extending through the bore 86 and the loading shaft 94. The loading shaft pin 100 is received by the slot 98 to limit range of motion of the loading shaft 94 relative to the second body 84. As described in greater detail further below, the slot 98 may assist the release assembly in moving the loading shaft 94 from the first load position to the second load position. The loading assembly 92 may comprise roller bearings 102 coupled to the loading shaft pin 100 and configured to engage the slot 98 to prevent friction between the loading shaft pin 100 and surfaces defining the slot 98.

As shown in FIGS. 12-15, the loading shaft 94 may define a channel 104 extending along the axis A and an aperture 106 in communication with the channel 104 and the bore 86 of the second body 84. The loading assembly 92 may include a push rod 108 disposed within the channel 104 and moveable along the axis A. The loading assembly 92 may further include a stopper 110 that may be at least partially received by the aperture 106. The push rod 108 and the stopper 110 cooperate to prevent movement of the loading shaft 94 along the axis A within the bore 86 of the second body 84. The push rod 108 may define a recess 112 configured to receive the stopper 110. The stopper 110 and the push rod 108 are configured to permit the loading shaft 94 to move relative to the second body 84 when the recess 112 of the push rod 108 receives the stopper 110.

The second body 84 may define a stopping groove 114 in communication with the bore 86 configured to receive the stopper 110. The push rod 108 is moveable along the axis A relative to the loading shaft 94 to a locked position (see FIGS. 12 and 13) where the stopper 110 is received in the aperture 106 of the loading shaft 94 and in the stopping groove 114 of the second body 84 to retain the loading shaft 94 in the second load position. The stopping groove 114 may be at least partially annular. The push rod 108 is moveable along the axis A relative to the loading shaft 94 to an unlocked position where the stopper 110 is received in the aperture 106 of the loading shaft 94 and in the recess 112 of the push rod 108 to permit the loading shaft 94 to move relative to the second body 84. When the push rod 108 moves from the locked position to the unlocked position, the loading shaft biasing member 96 urges the loading shaft 94 toward the first load position.

The push rod 108 is in the locked position in the second state of the loading assembly 92. The push rod 108 is in the unlocked position in the first state of the loading assembly 92. A push rod biasing member 116 may be disposed within the channel 104 and configured to bias the push rod 108 to the locked position. The push rod biasing member 116 can be any suitable biasing member, including, but not limited to: a compression spring, an extension spring, a coil spring, a helical spring, a leaf spring, a washer spring, a disc spring (e.g., Belleville disc spring), a piston (e.g., hydraulic, mechanical, or pneumatic), or the like. The push pin 82 interfaces the push rod 108 to move the push rod 108 from the locked position to the unlocked position. More specifically, as the first mounting portion 72 is being coupled to the second mounting portion 74, the push pin 82 abuts the push rod 108 to move the push rod 108 in opposition to the push rod biasing member 116 to the unlocked position. The push rod 108 may define a slot 118 for receiving a push rod pin 120 that is attached to the loading shaft 94 and extends through the channel 104 and the slot 118 to limit axial movement of the push rod 108 relative to the loading shaft 94.

Figure 18B:
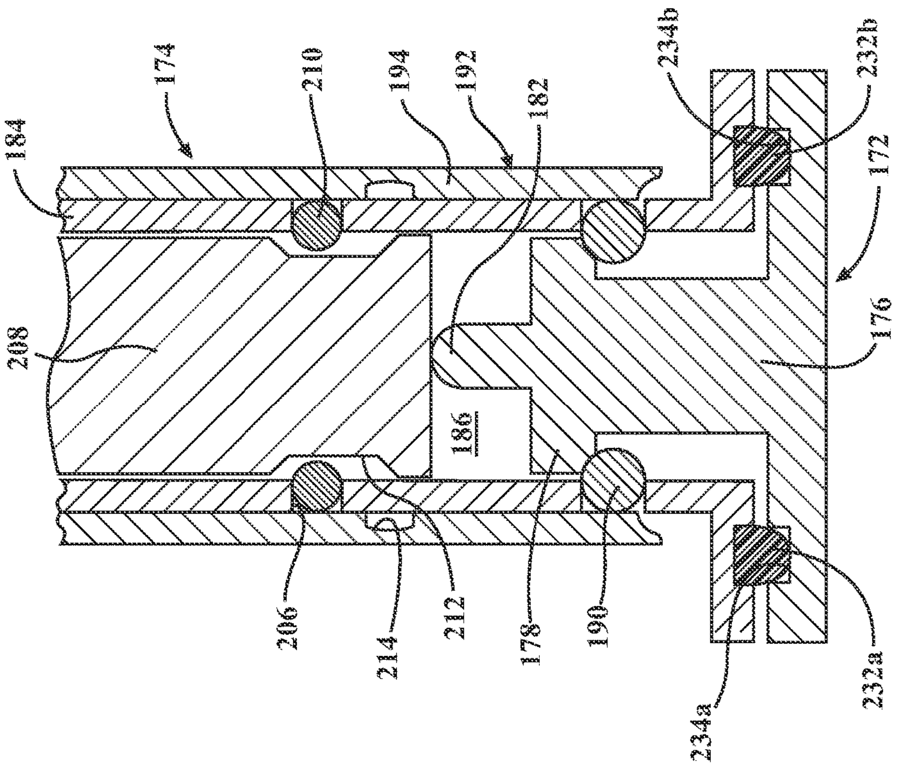
FIG. 18B is a partial sectional view of the alternative configuration of the first mounting portion being coupled to the alternative configuration of the second mounting portion, according to one implementation.
Figure 18A:
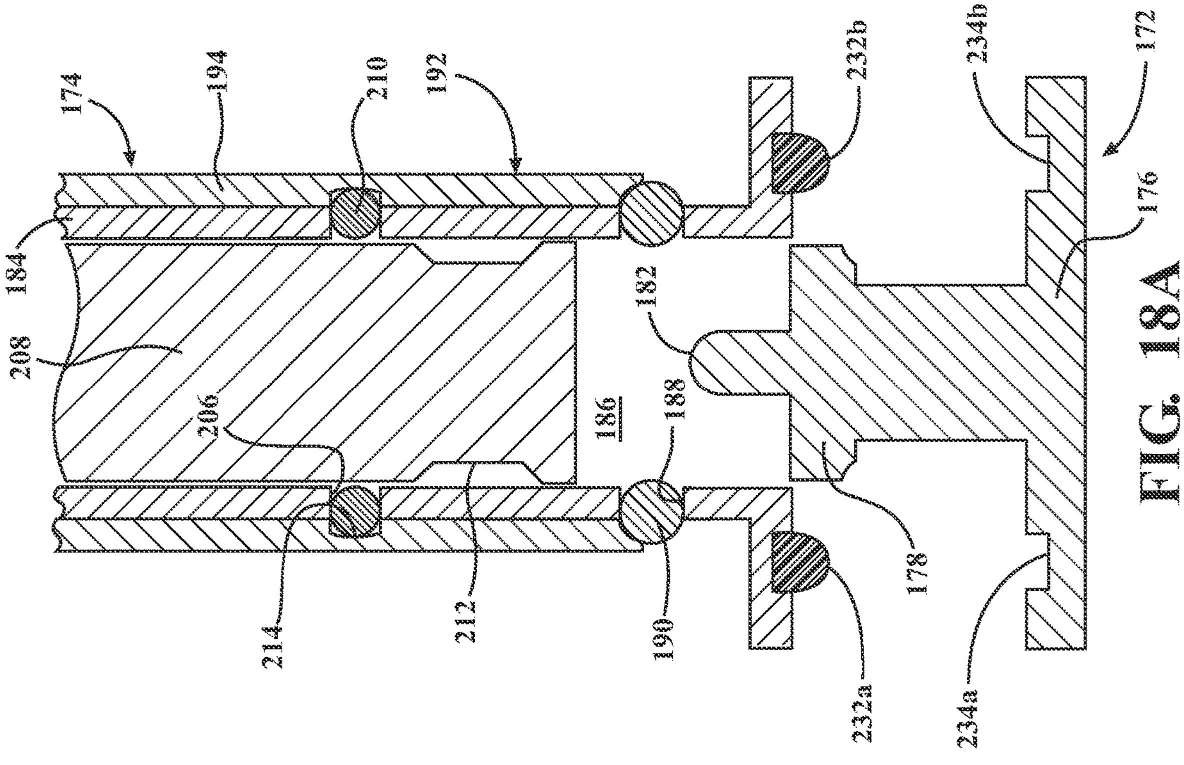
FIG. 18A is a partial sectional view of an alternative configuration of the first mounting portion being spaced from an alternative configuration of the second mounting portion, according to one implementation.

An alternative implementation of the first and second mounting portions 172, 174 is illustrated in FIGS. 18A and 18B. Unless otherwise noted, the components shown in FIGS. 18A and 18B may be the same as or similar to the components shown in preceding figures, except that the reference numbers are increased by 100. The second mounting portion 174 includes a loading assembly 192 disposed in communication with the bore 186 of the second body 184. The loading assembly 192 is moveable along the axis A to a first state (FIG. 18B) and a second state (FIG. 18A). In the first state (FIG. 18B), the first mounting portion 172 is secured to the second mounting portion 174. In the second state (FIG. 18A), the first mounting portion 172 may be separated from the second mounting portion 174. The loading assembly 192 is moveable in response to the push pin 182 interfacing the loading assembly 192 when the first mounting portion 172 is coupled to the second mounting portion 174. The loading assembly 192 is configured to move the retainers 190 to a coupling position in the first state. In the configuration of the coupling position illustrated in FIGS. 18B, each retainer 190 extends through one of the openings 188 beyond the inner surface of the second body 184. Each retainer 190 may extend beyond the inner surface of the second body 184 to abut the lip 178 of the first mounting portion 172 in the coupling position to secure the first mounting portion 172 to the second mounting portion 174. The loading assembly 192 permits the retainers 190 to move to a decoupling position in the second state. In the decoupling position, each retainer 190 may be farther from the axis A than in the coupling position. In some configurations, the retainers 190 in the decoupling position may be disposed within the openings 188 and outside the bore 186 and no part of any retainer 190 projects inwardly beyond the inner surface of the second body 184. In other configurations, the retainers 190 are permitted to extend within the bore 186 of the second body 184 less in the decoupling position than in the coupling position such that the retainers 190 do not abut the lip 178. In such a configuration, each retainer 190 in the decoupling position may project into the bore 186 beyond the inner surface of the second body 184 and still be disposed radially outward of the lip 178 to permit separation of the first mounting portion 172 from the second mounting portion 174.

As opposed to the preceding illustrated configurations, the loading assembly 192 of FIGS. 18A and 18B includes a loading shaft 194 disposed around the outer surface of the second body 184. The loading shaft 194 may be moveable along the axis A to a first load position (see FIG. 18B) in the first state of the loading assembly 192. In the first load position, the loading shaft 194 abuts the retainers 190 to move the retainers 190 to the coupling position. A proximal end of the loading shaft 194 may be tapered to assist in moving the retainers 190 inward in response to axial movement of the loading shaft 194. The proximal end may abut the retainers 190 to force the retainers 190 to the coupling position. The openings 188 of the second body 184 may be sized to prevent the retainers 190 from moving entirely inside of the bore 186 of the second body 184. The loading shaft 194 is moveable along the axis A to a second load position (see FIG. 18A) in the second state of the loading assembly 192. In the second load position, the loading shaft 194 permits each retainer 190 to move to the decoupling position.

The second body 184 may define an aperture 206 in communication with the bore 186 of the second body 184. The loading assembly 192 may include a push rod 208 disposed within the bore 186 and moveable along the axis A. The loading assembly 192 may further include a stopper 210 that may be at least partially received by the aperture 206. The push rod 208 and the stopper 210 cooperate to prevent movement of the loading shaft 194 along the axis A within the bore 186 of the second body 184. The push rod 208 may define a recess 212 configured to receive the stopper 210. The stopper 210 and the push rod 208 are configured to permit the loading shaft 194 to move relative to the second body 184 when the recess 212 of the push rod 208 receives the stopper 210.

The loading shaft 194 may define a stopping groove 214 in communication with the bore 186 configured to receive the stopper 210. The push rod 208 is moveable along the axis A relative to the second body 184 to a locked position (see FIG. 18A) where the stopper 210 is received in the aperture 206 of the second body 184 and in the stopping groove 214 of the loading shaft 194 to retain the loading shaft 194 in the second load position. The stopping groove 214 may be at least partially annular. The push rod 208 is moveable along the axis A relative to the second body 184 to an unlocked position where the stopper 210 is received in the aperture 206 of the second body 184 and in the recess 212 of the push rod 208 to permit the loading shaft 194 to move relative to the second body 184. When the push rod 208 moves from the locked position to the unlocked position, a loading shaft biasing member (not shown) urges the loading shaft 194 toward the first load position.

The push rod 208 is in the locked position in the second state of the loading assembly 192. The push rod 208 is in the unlocked position in the first state of the loading assembly 192. A push rod biasing member (not shown) may be disposed within the bore 186 and configured to bias the push rod 208 to the locked position. The push pin 182 interfaces the push rod 208 to move the push rod 208 from the locked position to the unlocked position. More specifically, as the first mounting portion 172 is being coupled to the second mounting portion 174, the push pin 182 abuts the push rod 208 to move the push rod 208 in opposition to the push rod biasing member to the unlocked position.

As shown in FIGS. 8-11, the second mounting portion 74 comprises a release assembly 122 coupled to the loading shaft 94. The release assembly 122 is configured to move the loading shaft 94 in opposition to the loading shaft biasing member 96 from the first load position to the second load position to permit the first mounting portion 72 to separate from the second mounting portion 74. The release assembly 122 comprises a head 124 being attached to the loading shaft 94. The head 124 is configured to be grasped by a user to move the loading shaft 94 from the first load position to the second load position. Owing to the slot 98 of the second body 84, the head 124 must be rotated to impart axial movement of the loading shaft 94 to move the loading shaft 94 from the first load position to the second load position. The second body 84 defines one or more locking grooves 126 adjacent a distal end of the second body 84. The release assembly 122 comprises a locking tab 128 rotatably coupled to the head 124. The locking tab 128 is moveable to a first locking tab position where the locking tab 128 abuts the second body 84 and engages the locking grooves 126 to prevent movement of the loading shaft 94 relative to the second body 84. The locking tab 128 is moveable to a second locking tab position different from the first locking tab position where movement of the loading shaft 94 relative to the second body 84 is permitted. The release assembly 122 comprises a locking tab biasing member 130 to bias the locking tab 128 to the first locking tab position. In the configurations illustrated in the figures, the release assembly 122 comprises two locking tabs 128. In one configuration the locking tab biasing member 130 comprises one or more spring loaded plungers. The locking tab biasing member 130 can be any suitable biasing member, including, but not limited to: a compression spring, an extension spring, a coil spring, a helical spring, a leaf spring, a washer spring, a disc spring (e.g., Belleville disc spring), a piston (e.g., hydraulic, mechanical, or pneumatic), or the like.

Figure 3:
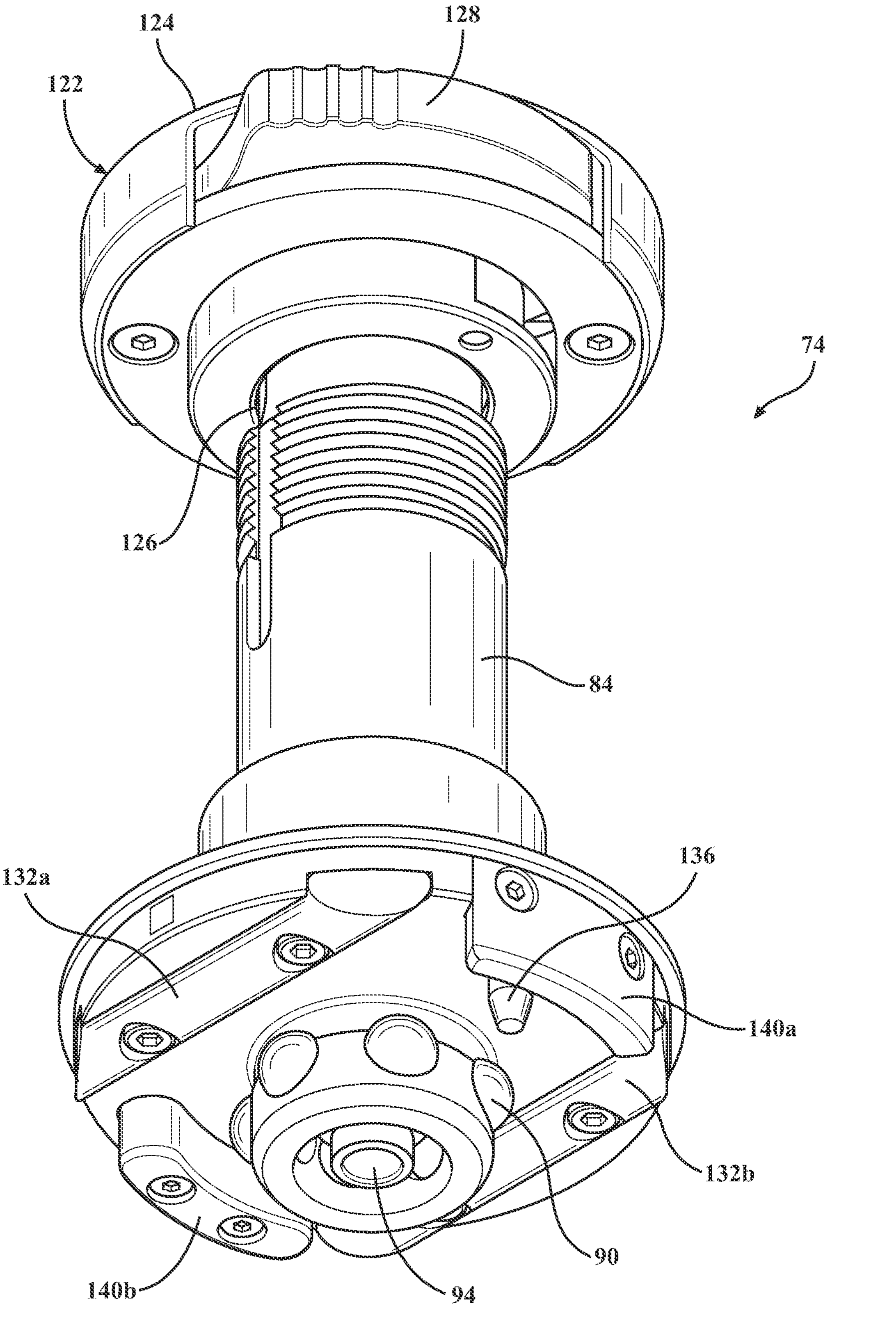
FIG. 3 is perspective view of a portion of the mounting system, according to one implementation.
Figure 4:
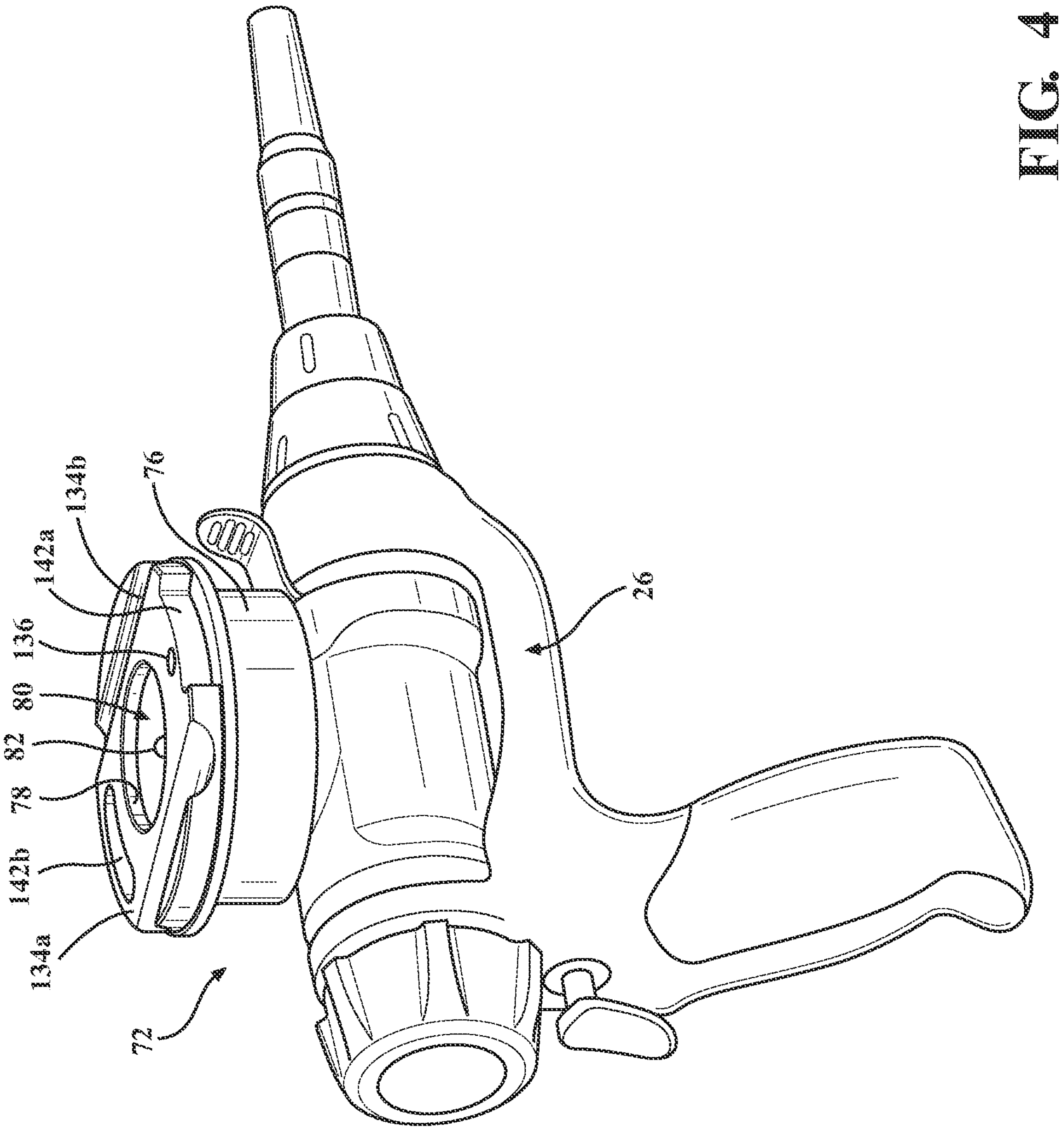
FIG. 4 is a perspective view of another portion of the mounting system and the end effector, according to one implementation.

As shown in FIGS. 3 and 4, the mounting system 70 may comprise a plurality of kinematic couplers coupled to one of the first and second mounting portions 72, 74 and configured to engage the other of the first and second mounting portions 72, 74 to provide a kinematic coupling between the mounting portions 72, 74 to constrain six degrees of freedom of movement between the mounting portions 72, 74 when the first mounting portion 72 is coupled to the second mounting portion 74. The kinematic couplers may include a first alignment bar 132*a* and a second alignment bar 132*b* coupled to the second body 84 of the second mounting portion 74. One of the first body 76 and the lip 78 of the first mounting portion 72 may define first and second alignment recesses 134*a*, 134*b* for receiving the first and second alignment bars 132*a*, 132*b*, respectively. The engagement between the alignment bars 132*a*, 132*b* and the alignment recesses 134*a*, 134*b* serve to eliminate five degrees of freedom. The kinematic couplers may also include an alignment post 136 extending from the second body 84 of the second mounting portion 74. One of the first body 76 and the lip 78 may define an alignment opening 138 to receive the alignment post 136 to cooperate with the alignment bars 132*a*, 132*b* in constraining six degrees of freedom. It is contemplated that kinematic coupling between the mounting portions 72, 74 may comprise the opposite configuration. It is also contemplated that kinematic coupling between the mounting portions 72, 74 to constrain six degrees of freedom of movement between the mounting portions 72, 74 when the first mounting portion 72 is coupled to the second mounting portion 74 may be achieved in other manners or by using other types of kinematic elements.

As shown in FIGS. 3 and 4, the mounting system 70 may also include physical or visual locators. In many configurations, visibility of the kinematic couplers may not be easily achieved. The locators may be more visible and prevent incorrect coupling of the first mounting portion 72 to the second mounting portion 74. For instance, the second mounting portion 74 may include first and second locating projections 140*a*, 140*b* extending from the second body 84 of the second mounting portion 74 to be received by first and second locating recesses 142*a*, 142*b* of one of the first body 76 and the lip 78 of the first mounting portion 72. The first and second locating projections 140*a*, 140*b*, and the respective first and second locating recesses 142*a*, 142*b* may be radially spaced apart from each other at different distances to provide keying and prevent incorrect coupling of the first mounting portion 72 to the second mounting portion 74. It is contemplated that instead of being radially spaced differently, the first and second locating projections 140*a*, 140*b* may have different sizes or be disposed at different angular orientations such that only a single orientation between the first and second mounting portions 72, 74 is permitted.

III. Mounting System Installation Examples

A sample configuration of coupling between the first and second mounting portions 72, 74 is shown in FIGS. 2 and 12-16D. A user may be attempting to secure the tool 26 to a link 18 of the manipulator 14 as illustrated in FIG. 2. The user begins with the first and second mounting portions 72, 74 spaced from each other as illustrated in FIG. 12 with the loading assembly 92 of the second mounting portion 74 in the second state. The user correctly aligns the first mounting portion 72 to the second mounting portion 74 using the locators and brings the push rod 108 into abutting engagement with the push pin 82. As the user brings the first mounting portion 72 toward the second mounting portion 74 such that the proximal end of the second body 84 is received deeper into the cup from the position shown in FIG. 13, the push pin 82 will move the push rod 108 toward the unlocked position in opposition to the push rod biasing member 116. The structural positioning of at least the push rod 108, push pin 82, retainers 90, and lip 78 may assist in coupling between the mounting portions 72, 74. For instance, if the push pin 82 engages the push rod 108 to move the push rod 108 to the unlocked position before the retainers 90 are received in the cavity 80 or abutting the lip 78, then the loading shaft biasing member 96 may force the retainers 90 to the coupling position before the retainers 90 are received within the cavity 80. In the second state, the locking tabs 128 are biased against the second body 84, but are not received in the locking grooves 126.

Figure 14:
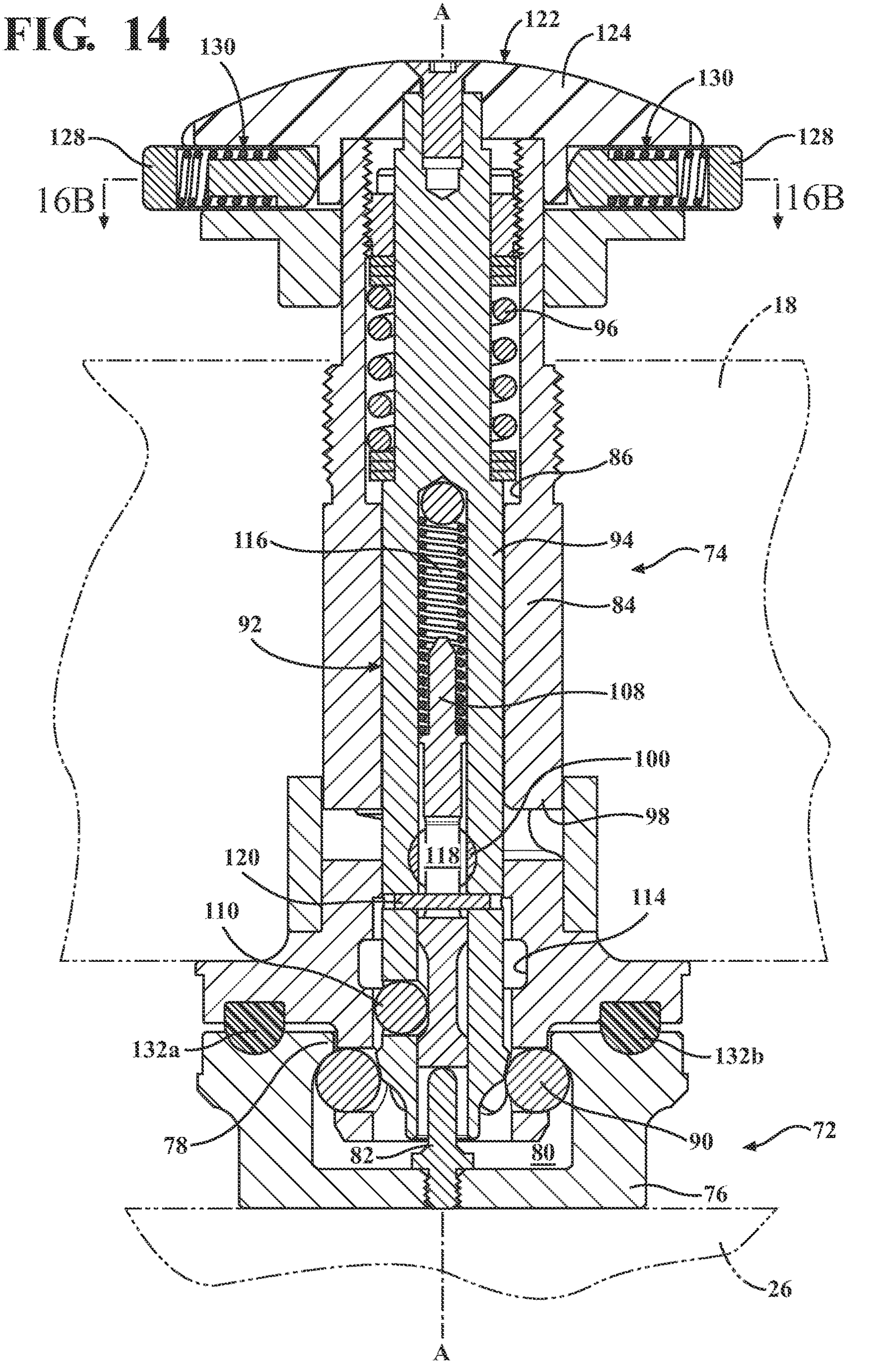
FIG. 14 is an elevational cross-section view of the mounting system in a third state, according to one implementation.
Figure 15:
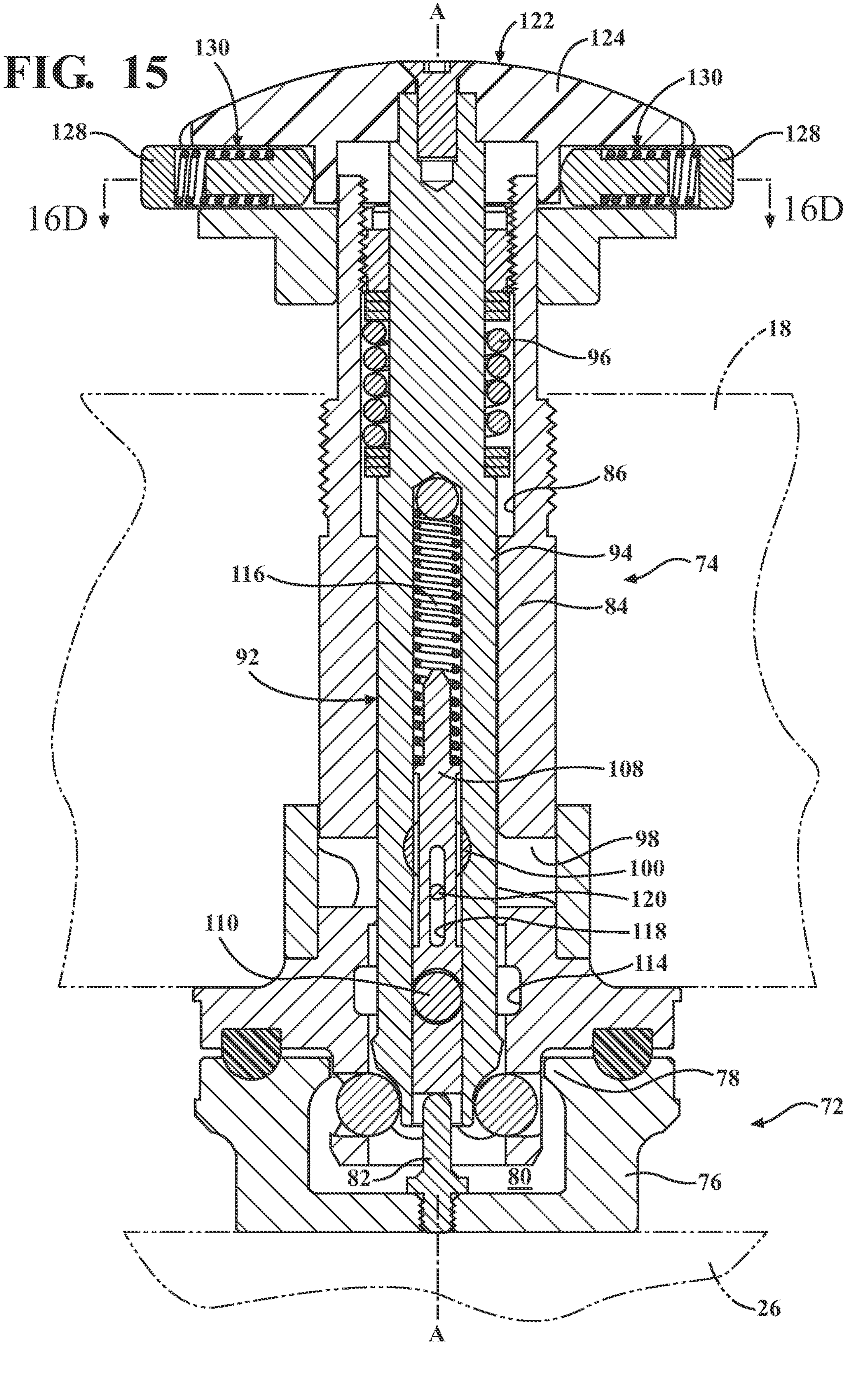
FIG. 15 is an elevational cross-section view of the mounting system in a fourth state, according to one implementation.
Figure 16A:
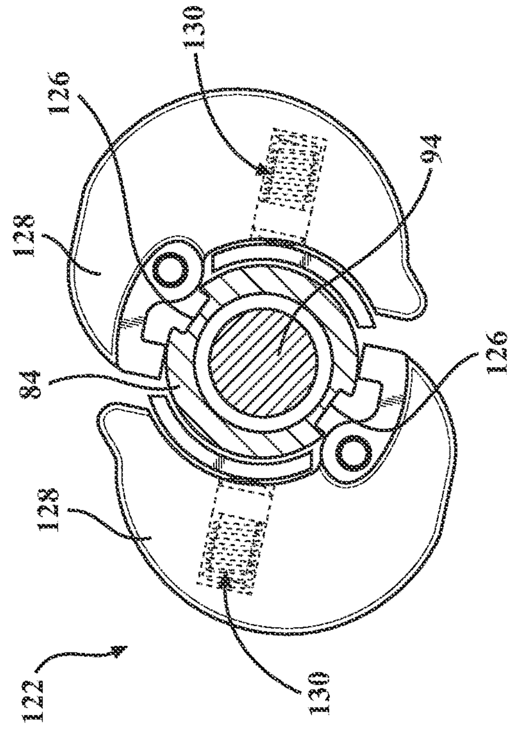
FIG. 16A is a sectional view of the release assembly, a loading assembly of the second mounting portion, and a body of the second mounting portion in a first configuration, according to one implementation.
Figure 16B:
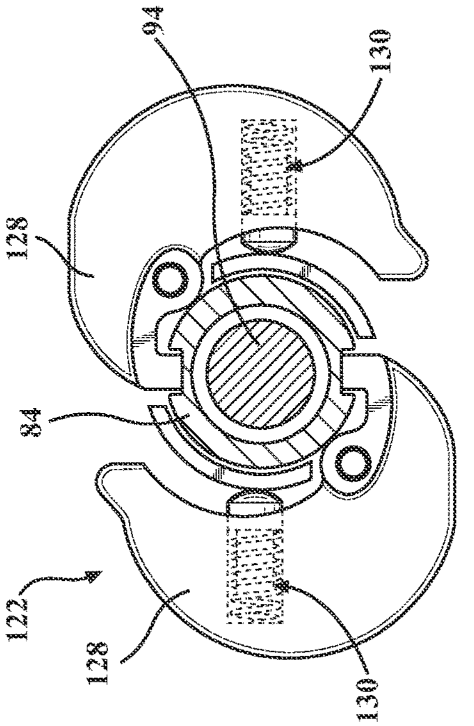
FIG. 16B is a sectional view of the release assembly, the loading assembly, and the body in a second configuration, according to one implementation.

As shown in FIGS. 14 and 16B, once the push rod 108 has moved to the unlocked position, the stopper 110 is removed from the stopping groove 114 and the loading shaft 94 is permitted to move relative to the second body 84. Unopposed, the loading shaft biasing member 96 moves the loading shaft 94 to the first load position. Movement of the loading shaft 94 to the first load position moves the retainers 90 to the coupling position engaging the lip 78. The spherical ball retainer 90 may engage the radius of the lip 78 with force from the loading shaft biasing member 96 to force the mounting portions 72, 74 together and keep tight engagement of the kinematic couplers between the mounting portions 72, 74. The loading assembly 92 of the second mounting portion 74 is in the second state and the secured to the first mounting portion 72. Owing to the slot 98, the loading shaft 94 is also rotated from the position shown in FIG. 16A so that the locking tabs 128 are aligned with and biased into the locking grooves 126 so that the locking tabs 128 are in the first locking tab position preventing rotational and axial movement of the loading shaft 94 relative to the second body 84.

Figure 16C:
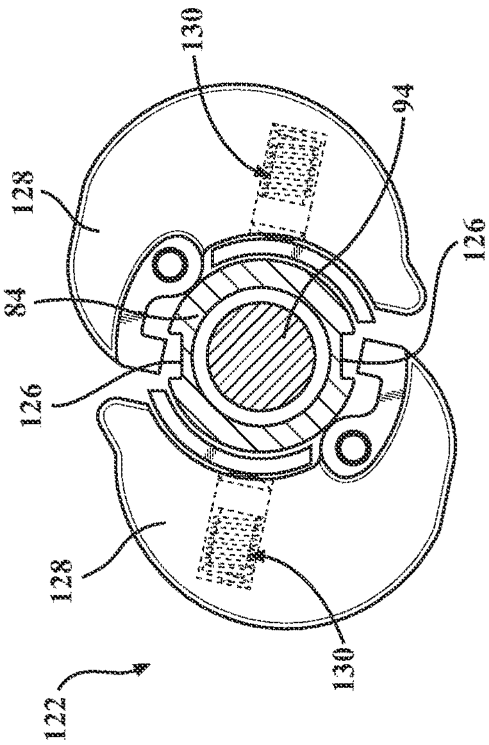
FIG. 16C is a sectional view of the release assembly, the loading assembly, and the body in a third configuration, according to one implementation.
Figure 16D:
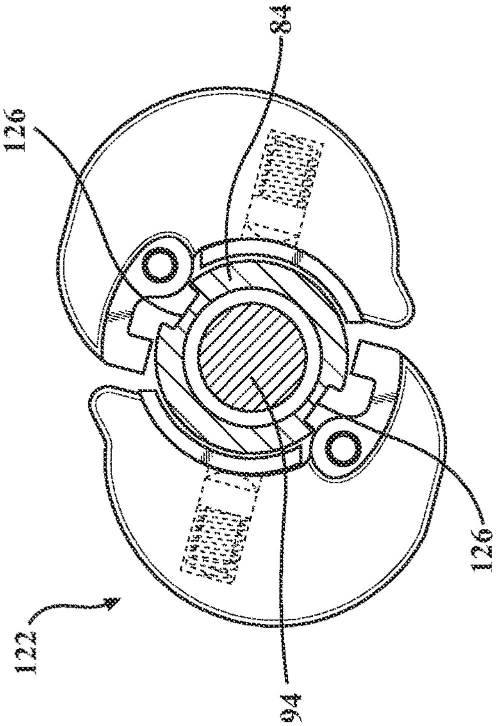
FIG. 16D is a sectional view of the release assembly, the loading assembly, and the body in a fourth configuration, according to one implementation.

To separate the first mounting portion 72 from the second mounting portion 74, the user first squeezes the locking tabs 128 to oppose the locking tab biasing members 130 and move the locking tabs 128 to the second locking tab position shown in FIG. 16C with the locking tabs 128 spaced from the second body 84. While the locking tabs 128 are out of the first locking tab position, the user then rotates the loading shaft 94 to the second load position shown in FIGS. 15 and 16D. Owing to the slot 98, the user opposes the loading shaft biasing member 96 while rotating the loading shaft 94 from the position shown in FIG. 16C to the position shown in FIG. 16D and moving the loading shaft 94 to the second load position with the push rod 108 in the unlocked position shown in FIG. 15. If the user releases their grip on the release assembly 122, the loading shaft biasing member 96 would return the loading shaft 94 to the first load position shown in FIG. 14. If the user continues to hold the release assembly 122 and separates the first mounting portion 72 from the second mounting portion 74, the push pin 82 will move away from the push rod 108 and the push rod biasing member 116 will move the push rod 108 to the locked position, forcing the stopper 110 into the stopping groove 114 and the loading assembly 92 of the second mounting portion 74 will be in the second state as shown in FIG. 12.

The structure of the second mounting portion 74, particularly the biasing members 96, 116, 130, assist in establishing a "quick-connect" coupling between the first mounting portion 72 and the second mounting portion 74. More specifically, coupling of the first mounting portion 72 to the second mounting portion 74 may be achieved with only alignment and axial movement of the first mounting portion 72 to the second mounting portion 74. In contrast, separating the first mounting portion 72 from the second mounting portion 74 requires more deliberate action (e.g., squeezing the locking tabs 128, rotating the loading shaft 94 against the loading shaft biasing members 96, etc.). In this manner, the risk of unintentionally decoupling the first mounting portion 72 from the second mounting portion 74 is mitigated.

Several configurations have been discussed in the foregoing description. However, the configurations discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

It will be further appreciated that the terms "include," "includes," and "including" have the same meaning as the terms "comprise," "comprises," and "comprising." Moreover, it will be appreciated that terms such as "first," "second," "third," and the like are used herein to differentiate certain structural features and components for the non-limiting, illustrative purposes of clarity and consistency.

What is claimed is:

1. A mounting system comprising:

a first mounting portion comprising: a first body, a lip extending from the first body, and a push pin extending from the first body and spaced from the lip; and a second mounting portion configured to be coupled with the first mounting portion, the second mounting portion comprising:

a second body extending along an axis, the second body having an outer surface and an inner surface, the inner surface defining a bore that extends along the axis, and the second body defining a plurality of openings through the inner and outer surfaces, a plurality of retainers, each retainer moveable within one of the openings relative to the second body in a direction perpendicular to the axis, and a loading assembly disposed within the bore of the second body, the loading assembly comprising a loading shaft, a stopper, and a push rod coupled to the loading shaft, wherein the loading shaft, the stopper, and the push rod are disposed within the bore of the second body, the loading shaft defining a channel along the axis to receive the push rod and an aperture to at least partially receive the stopper, the push rod defining a recess configured to at least partially receive the stopper, and the loading shaft being moveable along the axis to a first load position in response to the push pin interfacing the push rod to move the push rod axially relative to the loading shaft from a locked position in which the stopper is engageable with the second body through the aperture to restrain the loading shaft relative to the second body to an unlocked position in which the recess of the push rod is axially aligned in the channel with the stopper to permit the stopper to move radially inward in the aperture away from the second body to permit the loading shaft to move relative to the second body, wherein in the first load position, the loading shaft abuts the plurality of retainers to move the plurality of retainers to a coupling position whereby each retainer extends through one of the openings to abut the lip of the first mounting portion in the coupling position to secure the first mounting portion to the second mounting portion.

2. The mounting system of claim 1, wherein the loading shaft is moveable along the axis to a second load position, and wherein the loading shaft in the second load position permits the plurality of retainers to move to a decoupling position whereby the first mounting portion is permitted to separate from the second mounting portion.

3. The mounting system of claim 2, wherein each retainer in the coupling position extends through one of the openings beyond the outer surface of the second body, and wherein each retainer in the decoupling position is closer to the axis than in the coupling position.

4. The mounting system of claim 2, wherein the plurality of retainers in the decoupling position are disposed within the bore and no part of each retainer projects outwardly beyond the outer surface of the second body.

5. The mounting system of claim 1, wherein the second body defines a groove configured to receive the stopper, and wherein the push rod is moveable along the axis relative to the loading shaft to the locked position where the stopper is received in the aperture of the loading shaft and in the groove of the second body to retain the loading shaft in the second load position, and wherein the push rod is moveable along the axis relative to the loading shaft to the unlocked position where the stopper is received in the aperture of the loading shaft and in the recess of the push rod to permit the loading shaft to move relative to the second body.

6. The mounting system of claim 1, wherein the second body defines a slot extending about and along the axis, and wherein the loading assembly comprises a pin being attached to the loading shaft and extending through the bore and the loading shaft, the pin being received by the slot to limit range of motion of the loading shaft relative to the second body.

7. The mounting system of claim 1, wherein the second mounting portion comprises a release assembly coupled to the loading shaft of the loading assembly and configured to move the loading shaft from the first load position to a second load position to permit the first mounting portion to separate from the second mounting portion.

8. The mounting system of claim 7, wherein the release assembly comprises a head being attached to the loading shaft, the head configured to be grasped by a user to move the loading shaft from the first load position to the second load position.

9. The mounting system of claim 8, wherein the release assembly comprises a locking tab rotatably coupled to the head, the locking tab moveable to a first locking tab position where the locking tab abuts the second body to prevent movement of the loading shaft relative to the second body, and wherein the locking tab is moveable to a second locking tab position different from the first locking tab position where movement of the loading shaft relative to the second body is permitted.

10. The mounting system of claim 1, wherein the plurality of openings are defined about the axis, and wherein one or more of the plurality of retainers moves relative to the second body in a direction radial to the axis.

11. The mounting system of claim 10, wherein each retainer of the plurality of retainers is disposed radially inward of the lip to permit separation of the first mounting portion from the second mounting portion.

12. The mounting system of claim 1, wherein the first body and the lip collectively define a cavity, and wherein the push pin is disposed within the cavity.

13. The mounting system of claim 1, further comprising a plurality of kinematic couplers coupled to one of the first and second mounting portions and being configured to engage the other one of the first and second mounting portions to provide a kinematic coupling between the first and second mounting portions to constrain six degrees of freedom of movement between the first and second mounting portions when the plurality of retainers of the second mounting portion abut the lip of the first mounting portion.

14. The mounting system of claim 1, further comprising a first surgical component and a second surgical component, wherein the first mounting portion is coupled to the first surgical component and the second mounting portion is coupled to the second surgical component.

15. The mounting system of claim 14, wherein:

the first surgical component is any one of: a surgical navigation tracker, a surgical guide component, a powered surgical instrument component, a surgical hand tool component, a surgical robot component, a passive arm component, a surgical table component, and an imaging device component; and the second surgical component is any one of: a surgical navigation tracker, a surgical guide component, a powered surgical instrument component, a surgical hand tool component, a surgical robot component, a passive arm component, a surgical table component, and an imaging device component.

16. The mounting system of claim 1, wherein one or more of the plurality of openings are sized to prevent movement of one or more of the plurality of retainers to pass through the one or more of the openings.

17. A surgical system comprising:

a first surgical component, the first surgical component comprising any one of: a surgical navigation tracker, a surgical guide component, a powered surgical instrument component, a surgical hand tool component, a surgical robot component, a passive arm component, a surgical table component, and an imaging device component;

a second surgical component, the second surgical component comprising any one of: a surgical navigation tracker, a surgical guide component, a powered surgical instrument component, a surgical hand tool component, a surgical robot component, a passive arm component, a surgical table component, and an imaging device component; and a mounting system comprising:

a first mounting portion coupled to the first surgical component, the first mounting portion comprising: a first body, a lip extending from the first body, and a push pin extending from the first body and spaced from the lip; and a second mounting portion coupled to the second surgical component, the second mounting portion configured to be coupled with the first mounting portion, the second mounting portion comprising: a second body extending along an axis, the second body having an outer surface and an inner surface, the inner surface defining a bore that extends along the axis, and the second body defining a plurality of openings through the inner and outer surfaces, a plurality of retainers, each retainer moveable within one of the openings relative to the second body in a direction perpendicular to the axis, and a loading assembly disposed within the bore of the second body, the loading assembly comprising a loading shaft, a stopper, and a push rod coupled to the loading shaft, wherein the loading shaft, the stopper and the push rod are disposed within the bore of the second body, the loading shaft defining a channel along the axis to receive the push rod and an aperture to at least partially receive the stopper, the push rod defining a recess configured to at least partially receive the stopper, and the loading shaft being moveable along the axis to a first load position in response to the push pin interfacing the push rod to move the push rod axially relative to the loading shaft from a locked position in which the stopper is engageable with the second body through the aperture to restrain the loading shaft relative to the second body to an unlocked position in which the recess of the push rod is axially aligned in the channel with the stopper to permit the stopper to move radially inward in the aperture away from the second body to permit the loading shaft to move relative to the second body, wherein in the first load position, the loading shaft abuts the plurality of retainers to move the plurality of retainers to a coupling position whereby each retainer extends through one of the openings to abut the lip of the first mounting portion in the coupling position to secure the first mounting portion to the second mounting portion.

* * * * *